(12) United States Patent
Shtul et al.

(10) Patent No.: US 10,179,202 B2
(45) Date of Patent: Jan. 15, 2019

(54) SYSTEMS AND METHODS FOR CLEANING BODY CAVITIES AND FOR ENDOSCOPIC STEERING

(75) Inventors: Boris Shtul, Haifa (IL); Alexey Morochovsky, Haifa (IL); Alexander Banzger, Nesher (IL); Noam Hassidov, Moshav Bustan HaGalil (IL)

(73) Assignee: Motus GI Medical Technologies Ltd., Tirat HaCarmel (IL)

(*) Notice: Subject to any disclaimer, the term of this patent is extended or adjusted under 35 U.S.C. 154(b) by 1068 days.

(21) Appl. No.: 13/521,483

(22) PCT Filed: Jan. 11, 2011

(86) PCT No.: PCT/IB2011/050120
§ 371 (c)(1),
(2), (4) Date: Jul. 11, 2012

(87) PCT Pub. No.: WO2011/083450
PCT Pub. Date: Jul. 14, 2011

(65) Prior Publication Data
US 2013/0066297 A1    Mar. 14, 2013

Related U.S. Application Data

(60) Provisional application No. 61/354,226, filed on Jun. 13, 2010, provisional application No. 61/293,758, filed on Jan. 11, 2010.

(51) Int. Cl.
*A61M 3/02* (2006.01)
*A61B 1/015* (2006.01)
(Continued)

(52) U.S. Cl.
CPC .......... *A61M 3/0283* (2013.01); *A61B 1/015* (2013.01); *A61B 1/31* (2013.01); *A61M 1/0023* (2013.01);
(Continued)

(58) Field of Classification Search
CPC . A61B 1/015; A61B 1/04; A61B 1/31; A61M 1/0023; A61M 2210/1064; A61M 3/0283
See application file for complete search history.

(56) References Cited

U.S. PATENT DOCUMENTS 3,735,751 A    5/1973 Katz
4,117,847 A   10/1978 Clayton
(Continued)

FOREIGN PATENT DOCUMENTS

CN    1120805    4/1996
CN    1868554    11/2006
(Continued)

OTHER PUBLICATIONS

Office Action and Search Report dated Oct. 10, 2014 From the State Intellectual Property Office of the People's Republic of China Re. Application No. 201180013505.6 and Its Translation Into English.
(Continued)

*Primary Examiner* — Imani Hayman

(57) ABSTRACT

Systems and methods for cleaning body cavities are presented. Described embodiments include systems for cleaning feces from the lower GI tract. Also provided are systems for steering such a cleaning system, also useful for steering an endoscope or other tool inserted into a body.

28 Claims, 17 Drawing Sheets

(51) Int. Cl.
*A61B 1/31* (2006.01)
*A61F 5/445* (2006.01)
*A61M 1/00* (2006.01)
*A61M 16/04* (2006.01)
*A61F 5/442* (2006.01)
*A61B 17/3207* (2006.01)
*A61M 25/00* (2006.01)
*B08B 9/045* (2006.01)
*A61B 1/12* (2006.01)
*A61B 17/22* (2006.01)
*B08B 9/043* (2006.01)
*A61B 1/04* (2006.01)

(52) U.S. Cl.
CPC ............... *A61B 1/04* (2013.01); *A61B 1/122* (2013.01); *A61B 17/22012* (2013.01); *A61B 17/3207* (2013.01); *A61B 17/320758* (2013.01); *A61B 2217/005* (2013.01); *A61B 2217/007* (2013.01); *A61F 5/442* (2013.01); *A61F 5/445* (2013.01); *A61M 1/006* (2014.02); *A61M 1/008* (2013.01); *A61M 1/0035* (2014.02); *A61M 1/0084* (2013.01); *A61M 3/0275* (2013.01); *A61M 3/0295* (2013.01); *A61M 16/0463* (2013.01); *A61M 2025/0019* (2013.01); *A61M 2025/0025* (2013.01); *A61M 2205/3334* (2013.01); *A61M 2205/3389* (2013.01); *A61M 2210/1064* (2013.01); *B08B 9/045* (2013.01); *B08B 9/0436* (2013.01)

(56) References Cited

U.S. PATENT DOCUMENTS

| | | | |
|---|---|---|---|
| 4,257,422 | A | 3/1981 | Duncan |
| 4,445,509 | A | 5/1984 | Auth |
| 4,596,554 | A | 6/1986 | Dastgeer |
| 4,682,979 | A | 7/1987 | Girouard |
| 4,857,046 | A | 8/1989 | Stevens et al. |
| 4,874,363 | A | 10/1989 | Abell |
| 4,893,634 | A | 1/1990 | Kulik et al. |
| 4,902,276 | A | 2/1990 | Zakko |
| 5,019,056 | A | 5/1991 | Lee et al. |
| 5,047,040 | A | 9/1991 | Simpson et al. |
| 5,350,369 | A | 9/1994 | Workman et al. |
| 5,443,445 | A | 8/1995 | Peters et al. |
| 5,542,929 | A | 8/1996 | Laabs et al. |
| 5,630,795 | A | 5/1997 | Kuramoto et al. |
| 5,782,747 | A | 7/1998 | Zimmon |
| 5,788,650 | A | 8/1998 | Dotolo |
| 6,149,581 | A | 11/2000 | Klingenstein |
| 6,500,142 | B1 | 12/2002 | Harreld et al. |
| 6,595,971 | B1 | 7/2003 | Von Dyck et al. |
| 6,984,226 | B1 | 1/2006 | Abell et al. |
| 8,065,772 | B2 | 11/2011 | Maguire, Jr. et al. |
| 8,075,539 | B2 | 12/2011 | Nishtala et al. |
| 2002/0045852 | A1 | 4/2002 | Saab |
| 2003/0176833 | A1 | 9/2003 | Libermann |
| 2005/0004533 | A1 | 1/2005 | Smith |
| 2005/0054996 | A1 | 3/2005 | Gregory |
| 2005/0070933 | A1 | 3/2005 | Leiboff |
| 2005/0085694 | A1 | 4/2005 | Nakao |
| 2005/0096503 | A1 | 5/2005 | Conteas |
| 2005/0119628 | A1 | 6/2005 | Sant et al. |
| 2005/0148954 | A1 | 7/2005 | Abell |
| 2005/0261553 | A1 | 11/2005 | Swain et al. |
| 2006/0025728 | A1* | 2/2006 | Leiboff ............... A61M 3/0283 604/317 |
| 2006/0025729 | A1 | 2/2006 | Leiboff et al. |
| 2006/0173244 | A1 | 8/2006 | Boulais et al. |
| 2007/0015965 | A1 | 1/2007 | Cox et al. |
| 2007/0078444 | A1 | 4/2007 | Larsson |
| 2007/0244520 | A1 | 10/2007 | Ferren et al. |
| 2008/0097292 | A1 | 4/2008 | Cabiri et al. |
| 2008/0167606 | A1* | 7/2008 | Dann ............... A61M 25/0119 604/95.04 |
| 2008/0255596 | A1 | 10/2008 | Jenson et al. |
| 2008/0262308 | A1 | 10/2008 | Prestezog et al. |
| 2009/0143722 | A1 | 6/2009 | Kim |
| 2009/0264910 | A1 | 10/2009 | Laufer |
| 2011/0160657 | A1* | 6/2011 | Gobel ............... A61F 2/0013 604/96.01 |
| 2012/0253284 | A1 | 10/2012 | Nitsan et al. |
| 2012/0289892 | A1 | 11/2012 | Shtul et al. |
| 2012/0289910 | A1 | 11/2012 | Shtul et al. |
| 2013/0085442 | A1 | 4/2013 | Shtul et al. |
| 2013/0296771 | A1 | 11/2013 | Shtul et al. |

FOREIGN PATENT DOCUMENTS

| | | |
|---|---|---|
| CN | 101607100 | 12/2009 |
| DE | 8904403 | 7/1989 |
| EP | 1262205 | 12/2002 |
| EP | 2529779 | 12/2012 |
| JP | 02-191464 | 7/1990 |
| JP | 05-161711 | 6/1993 |
| JP | 2003-010324 | 1/2003 |
| WO | WO 88/00840 | 2/1988 |
| WO | WO 92/17219 | 10/1992 |
| WO | WO 94/18894 | 9/1994 |
| WO | WO 99/60934 | 12/1999 |
| WO | WO 2006/039511 | 4/2006 |
| WO | WO 2006/086826 | 8/2006 |
| WO | WO 2009/125387 | 10/2009 |
| WO | WO 2009/143201 | 11/2009 |
| WO | WO 2011/083450 | 7/2011 |
| WO | WO 2011/083451 | 7/2011 |
| WO | WO 2011/158232 | 12/2011 |

OTHER PUBLICATIONS

Communication Relating to the Results of the Partial International Search dated Jun. 6, 2011 From the International Searching Authority Re. Application No. PCT/IB2011/050121.
Communication Relating to the Results of the Partial International Search dated Nov. 15, 2011 From the International Searching Authority Re. Application No. PCT/IL2011/000470.
International Search Report and the Written Opinion dated Feb. 17, 2012 From the International Searching Authority Re. Application No. PCT/IL2011/000470.
International Search Report and the Written Opinion dated Aug. 18, 2011 From the International Searching Authority Re. Application No. PCT/IB2011/050121.
International Search Report and the Written Opinion dated Aug. 26, 2011 From the International Searching Authority Re: Application No. PCT/IB 11/50120.
Invitation to Pay Additional Fees dated Jun. 22, 2011 From the International Searching Authority Re. Application No. PCT/IB2011/50120.
Official Action dated Jun. 29, 2017 From the US Patent and Trademark Office Re. U.S. Appl. No. 13/557,371. (34 pages).
Applicant-Initiated Interview Summary dated Nov. 7, 2016 From the US Patent and Trademark Office Re. U.S. Appl. No. 13/703,986. (3 pages).
Official Action dated Dec. 15, 2016 From the US Patent and Trademark Office Re. U.S. Appl. No. 13/557,363. (29 pages).
Official Action dated Jan. 17, 2017 From the US Patent and Trademark Office Re. U.S. Appl. No. 13/557,371. (34 pages).
Official Action dated Dec. 30, 2016 From the US Patent and Trademark Office Re. U.S. Appl. No. 13/521,061. (31 pages).
Applicant-Initiated Interview Summary dated Feb. 3, 2017 From the US Patent and Trademark Office Re. U.S. Appl. No. 13/557,363. (4 pages).
International Preliminary Report on Patentability dated Jul. 26, 2012 From the International Bureau of WIPO Re. Application No. PCT/IB2011/050120.
International Preliminary Report on Patentability dated Jul. 26, 2012 From the International Bureau of WIPO Re. Application No. PCT/IB2011/050121.

(56) References Cited

OTHER PUBLICATIONS

International Preliminary Report on Patentability dated Dec. 27, 2012 From the International Bureau of WIPO Re. Application No. PCT/IL2011/000470.
Official Action dated Nov. 6, 2013 From the US Patent and Trademark Office Re. U.S. Appl. No. 13/557,371.
Restriction Official Action dated Dec. 19, 2013 From the US Patent and Trademark Office Re. U.S. Appl. No. 13/521,061.
Office Action and Search Report dated Jan. 17, 2014 From the State Intellectual Property Office of the People's Republic of China Re. Application No. 201180013505.6 and Its Summary in English.
Notification of Office Action dated Apr. 2, 2014 From the State Intellectual Property Office of the People's Republic of China Re. Application No. 201180039602.2 and Its Translation Into English.
Official Action dated May 21, 2014 From the US Patent and Trademark Office Re. U.S. Appl. No. 13/521,061.
Official Action dated Jul. 2, 2014 From the US Patent and Trademark Office Re. U.S. Appl. No. 13/557,371.
Examination Report dated Jul. 17, 2014 From the Instituto Mexicano de la Propiedad Industrial Re. Application No. MX/a/2012/008056 and Its Translation Into English.
Applicant-Initiated Interview Summary dated Nov. 14, 2014 From the US Patent and Trademark Office Re. U.S. Appl. No. 13/557,371.
Notice of Reason for Rejection dated Nov. 7, 2014 From the Japanese Patent Office Re. Application No. 2012-548515 and Its Translation Into English.
Notification of Office Action and Search Report dated Nov. 24, 2014 From the State Intellectual Property Office of the People's Republic of China Re. Application No. 201180039602.2.
Official Action dated Dec. 15, 2014 From the US Patent and Trademark Office Re. U.S. Appl. No. 13/521,061.
Translation Dated Dec. 10, 2014 of Notification of Office Action and Search Report dated Nov. 24, 2014 From the State Intellectual Property Office of the People's Republic of China Re. Application No. 201180039602.2.
Applicant-Initiated Interview Summary dated Mar. 20, 2015 From the US Patent and Trademark Office Re. U.S. Appl. No. 13/521,061.
Notice of Reason for Rejection dated Mar. 20, 2015 From the Japanese Patent Office Re. Application No. 2013-514838 and Its Translation Into English.
Restriction Official Action dated Jun. 26, 2015 From the US Patent and Trademark Office Re. U.S. Appl. No. 13/703,986.
Official Action dated Sep. 15, 2015 From the US Patent and Trademark Office Re. U.S. Appl. No. 13/557,371.
Restriction Official Action dated Nov. 16, 2015 From the US Patent and Trademark Office Re. U.S. Appl. No. 13/557,363.
Official Action dated Dec. 30, 2015 From the US Patent and Trademark Office Re. U.S. Appl. No. 13/703,986.
Official Decision of Rejection dated Feb. 2, 2016 From the Japanese Patent Office Re. Application No. 2013-514838 and Its Translation Into English.
Official Action dated Mar. 24, 2016 From the US Patent and Trademark Office Re. U.S. Appl. No. 13/521,061.
Official Action dated Mar. 24, 2016 From the US Patent and Trademark Office Re. U.S. Appl. No. 13/557,371.
Official Action dated Jun. 2, 2016 From the US Patent and Trademark Office Re. U.S. Appl. No. 13/557,363.
Official Action dated Jun. 23, 2016 From the US Patent and Trademark Office Re. U.S. Appl. No. 13/703,986.
Communication Pursuant to Article 94(3) EPC dated Jul. 12, 2016 From the European Patent Office Re. Application No. 11732520.9.
Applicant-Initiated Interview Summary dated Feb. 16, 2017 From the US Patent and Trademark Office Re. U.S. Appl. No. 13/557,371. (4 pages).
Notice of Reason for Rejection dated Dec. 1, 2017 From the Japan Patent Office Re. Application No. 2016-110785 and Its Translation Into English. (11 Pages).
Advisory Action Before the Filing of an Appeal Brief dated Feb. 22, 2018 From the US Patent and Trademark Office Re. U.S. Appl. No. 13/703,986. (3 pages).
Notice of Reason for Rejection dated Mar. 23, 2018 From the Japan Patent Office Re. Application No. 2016-110785 and Its Translation Into English. (4 Pages).
Applicant-Initiated Interview Summary dated Aug. 31, 2018 From the US Patent and Trademark Office Re. U.S. Appl. No. 13/557,363. (3 pages).
Communication Pursuant to Article 94(3) EPC dated Sep. 25, 2018 From the European Patent Office Re. Application No. 11731727.1. (6 Pages).
Official Action dated Sep. 5, 2018 From the US Patent and Trademark Office Re. U.S. Appl. No. 13/703,986. (38 pages).
Official Action dated Jul. 13, 2018 From the US Patent and Trademark Office Re. U.S. Appl. No. 13/557,363. (30 pages).
Communication Pursuant to Article 94(3) EPC dated Jul. 5, 2016 From the European Patent Office Re. Application No. 11703037.9.
Supplementary European Search Report and the European Search Opinion dated Mar. 29, 2017 From the European Patent Office Re. Application No. 11731727.1. (9 Pages).
Applicant-Initiated Interview Summary dated Apr. 13, 2017 From the US Patent and Trademark Office Re. U.S. Appl. No. 13/703,986. (3 pages).
Notice of Reason for Rejection dated Mar. 31, 2017 From the Japan Patent Office Re. Application No. 2016-110785 and Its Translation Into English. (8 Pages).
Official Action dated Feb. 13, 2017 From the US Patent and Trademark Office Re. U.S. Appl. No. 13/703,986. (31 pages).
Official Action dated Sep. 15, 2017 From the US Patent and Trademark Office Re. U.S. Appl. No. 13/557,363. (27 pages).
Official Action dated Aug. 24, 2017 From the US Patent and Trademark Office Re. U.S. Appl. No. 13/703,986. (18 pages).
Applicant-Initiated Interview Summary dated Mar. 21, 2017 From the US Patent and Trademark Office Re. U.S. Appl. No. 13/557,363. (6 pages).

* cited by examiner

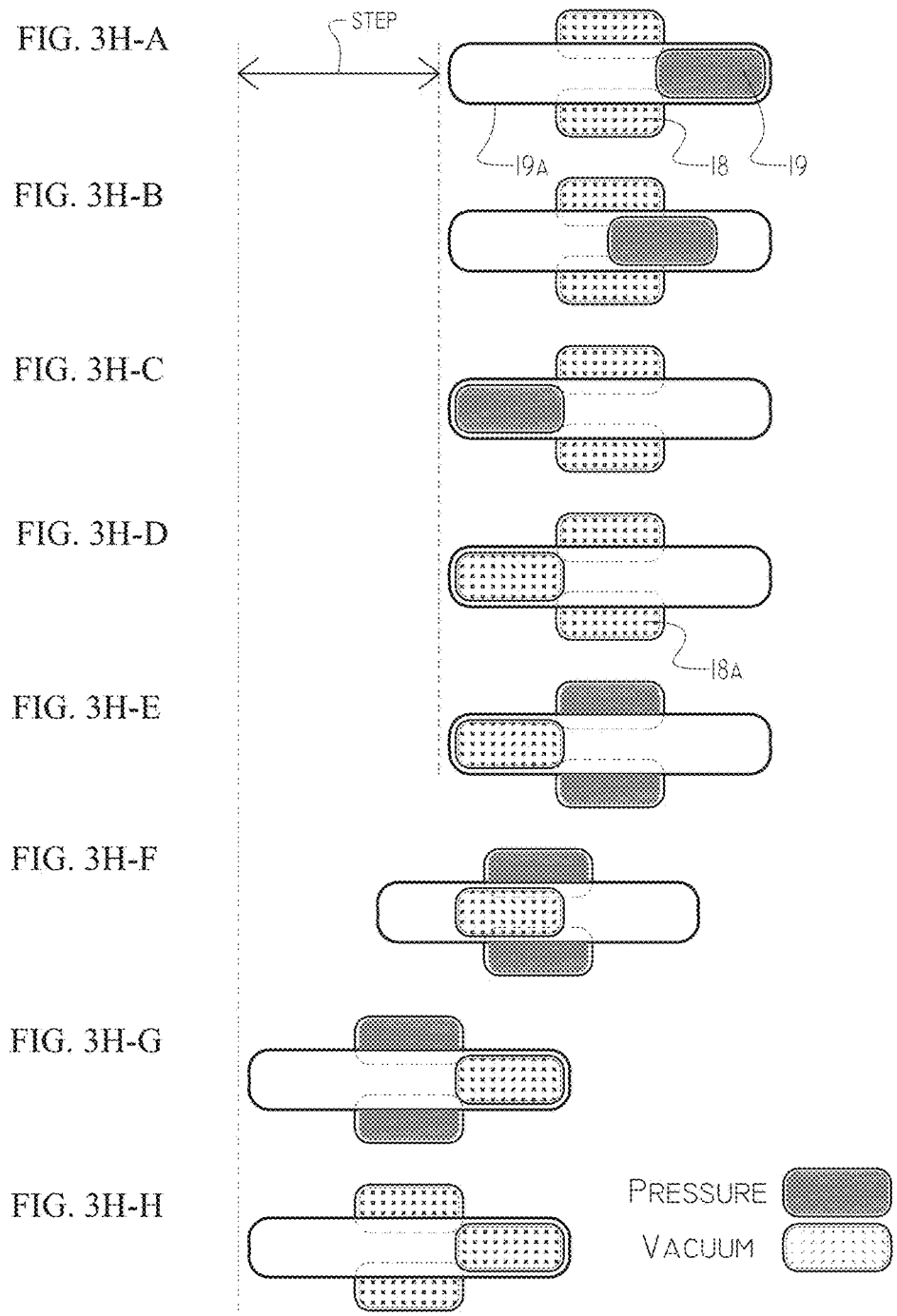

SYSTEMS AND METHODS FOR CLEANING BODY CAVITIES AND FOR ENDOSCOPIC STEERING

RELATED APPLICATIONS

This application is a National Phase of PCT Patent application No. PCT/IB2011/050120 having International filing date of Jan. 11, 2011, which claims the benefit of priority under 35 USC § 119 (e) of U.S. Provisional Application Nos. 61/293,758 filed on Jan. 11, 2010 and 61/354,226 filed on Jun. 13, 2010. PCT Application No. PCT/IB2011/050120 was co-filed with PCT Application No. PCT/IB2011/050121 having International filing date of Jan. 11, 2011. The contents of the above applications are all incorporated by reference as if fully set forth herein in their entirety.

FIELD AND BACKGROUND OF THE INVENTION

The present invention, in some embodiments thereof, relates to a system for cleaning body conduits and/or body cavities, and more particularly, but not exclusively, to a system for cleaning the lower GI tract. The present invention, in some embodiments thereof, also relates to systems and methods for endoscopic steering.

The well-known enema has a long history as a system for cleaning the colon. An enema is a tube inserted into the lower colon through the rectum, and used to inject water or other liquids into the colon. Cleaning is achieved when the injected liquid, mixed with fecal matter, is ejected from the body by natural processes.

More recently, closed hydrotherapy (or cleansing) systems have been introduced, wherein a liquid source tube, optionally capable of supplying liquid under low pressure, is paired with an evacuation tube. In a first phase of the cleansing cycle liquids flow from the rectum up the colon due to the low pressure and fill the colon cavity, dissolving and/or causing the feces to fall apart; in a second phase of the cleansing cycle the mixtures of liquid and fecal matter can then be evacuated from the bowel through the evacuation tube. In similarity to the enema, the speculum of such systems is usually introduced approximately 6-8 centimeters into the body. An example is shown at wwwdotdotolore-searchdotcom.

A colonoscope (a hand-driven flexible endoscope able to reach further into the lower GI system, up to the cecum) may be used to clean local fecal deposits, by locally spraying water and exhausting feces. However, the gold standard is first performing a body cleansing and then cleaning up only small remainders during a colonoscopic procedure.

An additional solution is to provide an add-on for a colonoscope that comprises large bore working channel used to evacuate feces, and several irrigation pipes bundled together. wwwdoteasy-glidedotcom shows an add-on for a colonoscope including a working channel to evacuate feces and several irrigation pipes bundled therewith.

Additional art which may be relevant includes PCT WO2008/155776 A1 and WO2009/143201 A1.

SUMMARY OF THE INVENTION

The present invention, in some embodiments thereof, relates to a system for cleaning body cavities and for transporting material in and out of body cavities, in particular the colon. In an exemplary embodiment of the invention, a cleaning/evacuating system includes a means for wetting fecal matter (e.g., by spraying or irrigation) and means for removing fecal matter which is broken up by the wetting.

There is provided in accordance with exemplary embodiments of the invention, an envelope for colonic cleaning, comprising:
  a body including a fecal container of at least 2 liters volume;
  an anal seal adapted to seal to an anus; and
  a proximal seal adapted to seal to a colon insertion tube.

In an exemplary embodiment of the invention, said envelope is formed of a flexible material. Optionally or alternatively, said envelope is an integral piece.

In an exemplary embodiment of the invention, said anal seal includes a speculum which defines an inner lumen larger in diameter than an outer diameter of the colon insertion tube. Optionally or alternatively, said proximal seal is a sliding seal. Alternatively, said proximal seal is a fixed attachment to said insertion tube.

In an exemplary embodiment of the invention, the envelope includes a vertical sleeve connecting to said fecal container.

In an exemplary embodiment of the invention, said body includes at least one pleated section.

In an exemplary embodiment of the invention, the envelope comprises a sensor operative to measure an amount of contents of said container. Optionally, the envelope comprises a valve operative to change the flow of a liquid responsive to said measured amount.

There is provided in accordance with exemplary embodiments of the invention, a colon cleaning tracking system, comprising:
  a container for collecting feces; and
  at least one senor for generating a signal responsive to an amount of material in said container. Optionally, said sensor is a scale. Optionally or alternatively, the system comprises at least one valve and circuitry which controls said valve responsive to said sensor signal.

There is provided in accordance with exemplary embodiments of the invention, a method of monitoring a colon cleaning operation, comprising:
  providing fluid into the colon;
  collecting an exhaust from the colon;
  sensing an amount of exhaust; and
  automatically controlling said providing responsive to said measuring.

There is provided in accordance with exemplary embodiments of the invention, a method of cleaning the colon, comprising:
  Attaching an envelope to an anus;
  Providing a fluid through said envelope into said anus; and
  collecting exhaust from said anus into said envelope.

There is provided in accordance with exemplary embodiments of the invention, a method of exhausting a colon, comprising:
  advancing an elongate element with a plurality of vanes thereof into an exhaust conduit;
  opening the veins to block part of the conduit; and
  retracting the elongate element.

There is provided in accordance with exemplary embodiments of the invention, apparatus for colon cleaning, comprising:
  a tube adapted for insertion into a colon and defining an exhaust lumen;
  an elongate element located within said exhaust lumen and movable axially for at least a distance of 2 cm; and at least one vane rotatably mounted on said elongate element, to selectively block or unblock part of said lumen. Optionally, said veins are spring-loaded to open.

There is provided in accordance with exemplary embodiments of the invention, a medical insertion tube steering mechanism, comprising:
a body;
a head;
a plurality of interconnection elements interconnecting said head and said body,
wherein at least one of said element is a hollow tube configured for passage or material out of said tube and wherein at least one of said interconnection elements is movable so as to reorient said head relative to said body. Optionally, the mechanism comprises at least two hollow tubes. Optionally or alternatively, said tube is flexible enough to allow said head to be deflected relative to said body when said head contacts a wall of the GI tract.

There is provided in accordance with exemplary embodiments of the invention, a method of colon cleaning, comprising providing a cylindrical element into the colon, which element has a plurality of apertures at its distal end and which tube is configured to resist radial compression by body parts. Optionally, the method comprises using said tube for insertion of a fluid into said colon.

There is provided in accordance with exemplary embodiments of the invention, apparatus for colon cleaning, comprising:
at least one tube for insertion into a colon and including a liquid outlet into the colon;
at least one radially resilient cylindrical element enclosing said at least one tube. Optionally, said resilient element defines a plurality of apertures at a distal end thereof.

There is provided in accordance with exemplary embodiments of the invention, a method of colon cleaning, comprising using a same tube to insert liquid and remove feces from a colon.

There is provided in accordance with exemplary embodiments of the invention, apparatus for exhausting a colon, comprising:
an exhaust conduit adapted for insertion into a colon;
a rotating exhausting element mounted within said exhaust conduit; and
a distal stop for preventing axial distal advance of said rotating element.

In an exemplary embodiment of the invention, said rotating element comprises a spiral element with axial elasticity. Optionally or alternatively, said spiral element is configured to shred fecal matter. Optionally or alternatively, said spiral element defines spacings between adjacent coil turns, which spacings are uneven. Optionally or alternatively, said spiral element defines a diameter of adjunct coil turns, which diameters are unequal.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein may be performed by a "controller", which may comprise a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3H-A to 3H-H, and 3I and 3J are simplified schematics of a locomotion system for use with any of the embodiments presented herein, according to some embodiments of the present invention;

DESCRIPTION OF SPECIFIC EMBODIMENTS OF THE INVENTION

Figure 1A:
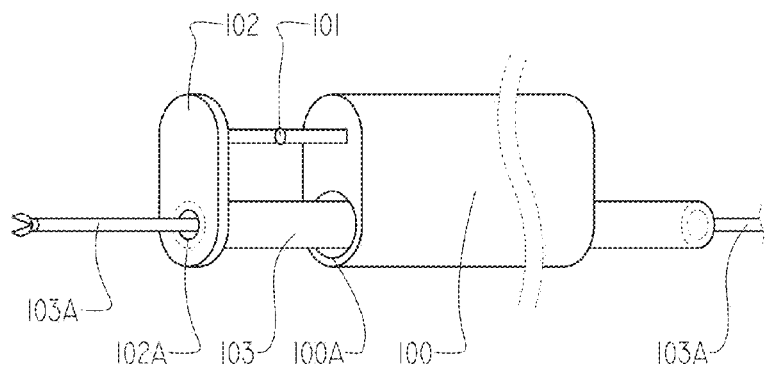
FIGS. 1A-1N are simplified schematics of endoscopic steering systems, according to some embodiments of the present invention.

The present invention, in some embodiments thereof, relates to a system for cleaning body cavities and for transporting material in and out of body cavities, in particular the colon. In an exemplary embodiment of the invention, a cleaning/evacuating system includes a means for wetting fecal matter (e.g., by spraying or irrigation) and means for removing fecal matter which is broken up by the wetting.

In an exemplary embodiment of the invention, the means for removing includes an exhaust conduit which is optionally designed to resist compression so as to provide an exhaust pathway resistance to blockage by being compressed from the outside.

In an exemplary embodiment of the invention, the system has a medial tube body (also known as Speculum for colonic uses) insertable into a body conduit such as a patient's intestine. The system also optionally comprises a proximal base.

In some exemplary embodiments of the invention, colon cleaning and/or evacuation systems are designed for mounting on an endoscope. In alternative embodiments, such a system is integral to an endoscope or is provided separately into the body. Optionally or alternatively, a colon cleaning system is includes one or more light sources and/or imaging elements.

In some embodiments of the invention, the cleaner is mounted on or integral with a locomotor module (e.g., self-advancing endoscope or other device) operable to displace the cleaner within the body conduit.

In some of the embodiments, including, without limitation, embodiments with self-locomoting or hand-driven cleaners, the cleaner's direction of advance and/or the direction of liquid spray by liquid spray nozzles or of an entrances to an exhaust conduit for evacuating materials is steerable by a user operating a steering mechanism controlled from outside the body.

Some embodiments of the invention comprise several of the features described herein in combination, and provide cleaning systems requiring little patient preparation. Some embodiments provide systems for cleaning together with systems for imaging and/or for manipulation (e.g. biopsy), so that two or more of cleaning, imaging, and/or manipulation can be undertaken using a single device and a single intervention.

In an exemplary embodiment of the invention, for the colon, the outer diameter of a system is between 0.5 and 4 cm, for example, between 1 and 2.5 cm. In an exemplary embodiment of the invention, the length of a tube inserted into the colon is between 0.5 and 4 meters, for example, between 1 and 2.5 meters. Optionally, apertures are sized for receiving fecal pieces of diameter between 0.2 and 3 cm, for example, between 0.5 and 2 cm in diameter. Optionally, apertures are sized less than 4 cm, or less than 3 or 2 or 1 cm or intermediate sizes, to reduce the possibility and extent of intestinal protrusion therethrough. Optionally, moving parts are located, for example, 1 cm, 2 cm, 3 cm or more or intermediate distances from apertures.

An aspect of some embodiments of the invention relates to a steering mechanism for a tubular element in the body, in which a part of the steering mechanism is hollow and can act as a lumen for, for example, evacuation, liquid provision and/or tool provision. In an exemplary embodiment of the invention, the tube acts as one of a plurality of elements interconnecting a base and a head of the tube. In an exemplary embodiment of the invention, the tube is advanced and/or retreated in order to cause the head of the tube to reorient relative to the base. Optionally or alternatively, one or more tension elements and/or compression elements (e.g., rods or cables) are manipulated and act as one or more of said plurality of elements, causing the tube to bend. Optionally or alternatively, advancing of the tube causes an interconnecting element to bend.

Optionally, one or more of the interconnecting elements is elastic, providing spring-back of the head to a forward looking (or other) base position.

In an exemplary embodiment of the invention, at least one of the interconnecting elements is flexible enough so that when the tube hits an obstacle, the head can bend, rather than cause a penetration of an obstacle. Flexibility of the tubes can enable the tubes to provide for 'self navigation' of the device, meaning that the head is directable, yet flexible enough to yield to pressures imposed by conduit walls as the device is advanced through the sometimes complex geometry of a body conduit. In one example, hollow directing tubes constructed of materials with high flexibility, such as silicone, Tygon, Teflon, and polyurethane, are used.

An aspect of some embodiments of the invention relates to a colon evacuating system including one or more mechanisms for mechanically breaking down (e.g., shredding) fecal matter so that it can be more easily evacuated. A potential advantage of such systems is that they may be better able to deal with undissolvable components of fecal matter, such as undigested food parts (e.g. corn seeds), which might otherwise impede throughput by clogging up the entrances to and/or the passageway of the exhaust conduit, impeding or preventing functioning of the apparatus. Optionally, a matter-shredding mechanism for shredding matter or otherwise dividing pieces of matter into smaller pieces may also serve for evacuation of the exhaust conduit.

An aspect of some embodiments of the invention relates to a colon evacuating system including a mechanism for mechanically conveying fecal matter out of the body. In an exemplary embodiment of the invention, the mechanism includes a plurality of vanes or flaps that are opened or closed and then retracted from an exhaust tube with fecal matter trapped thereby.

An aspect of some embodiments of the invention relates to a colon evacuating system which includes a single tube that functions both to inject a liquid into the body cavity, and to exhaust liquid and matter from that body cavity. The tube may comprise a mechanism for shredding and/or transporting matter.

An aspect of some embodiments of the invention relates to a colon support element which prevents collapsing of the GI tract onto an exhaust channel and/or onto an endoscope in a manner which prevents flow therepast. In an exemplary embodiment of the invention, the support comprises a tube.

Optionally, the tube has a plurality of openings formed therein, for ingress of fecal matter thereto. Optionally or alternatively, the support comprises a coil.

An aspect of some embodiments of the invention relates to a containment system for a colon cleaning system. In an exemplary embodiment of the invention, the containment system includes a sealed envelope that is sealed, at one end to a speculum that is inserted into the anus and at another end to a collection container. In an exemplary embodiment of the invention, the envelope is includes a portion which covers a colonoscope (or other tube for insertion into the colon through the speculum). Optionally, the potion is axially extendible, for example, being pleated, so as to change its length according to the insertion depth of the colonoscope. Optionally, the envelope is sealed to a proximal part of the colonoscope. Optionally or alternatively, the envelope includes the tube for insertion into and evacuating the colon. In an exemplary embodiment of the invention, the tube is coupled to a water reservoir, optionally also provided as part of the envelope. Optionally, the envelope includes a scale for measuring the inflow and outflow and optionally controlling circuitry for stopping inflow and/or increasing outflow according to thresholds of allowed differences.

An aspect of some embodiments of the invention relates to using a scale for controlling a colon irrigation and/or cleaning system. In an exemplary embodiment of the invention, a scale or pressure sensor or other mechanism is used to gauge the amount of material removed from a colon. A sensor, such as a flow rate sensor may be used to gauge the rate or amount of inflow. If the outflow is not high enough, inflow is optionally automatically stopped or slowed down, to avoid over filling the colon. Optionally or alternatively, colon evacuation means, such as a pump, may be activated or increase in activation. Optionally or alternatively, an alert is shown to a user, as potentially indicating a blockage of the system.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Flexible Steering

Figure 1B:
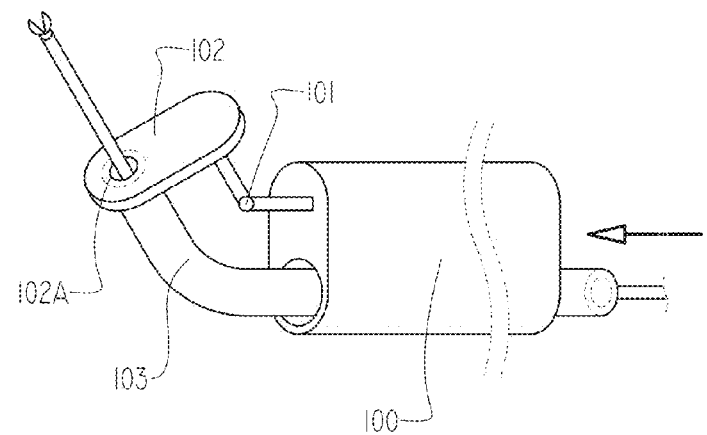
Figure 1C:
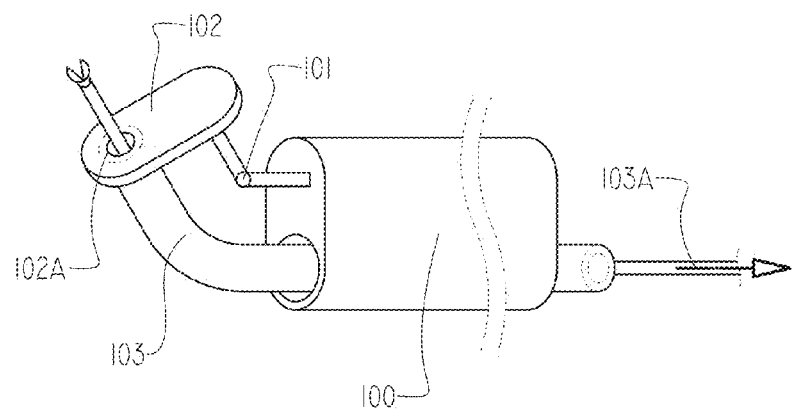
Figure 1D:
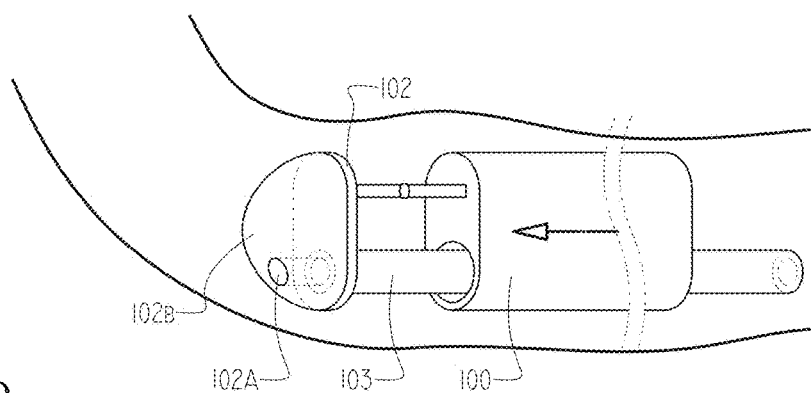
Figure 1E:
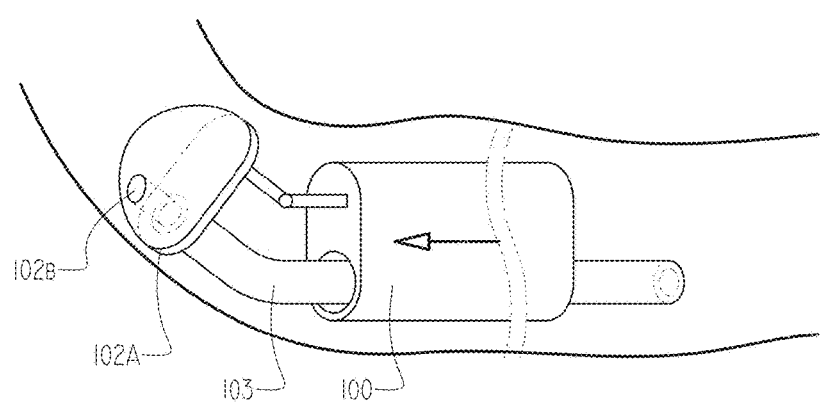
Figure 1F:
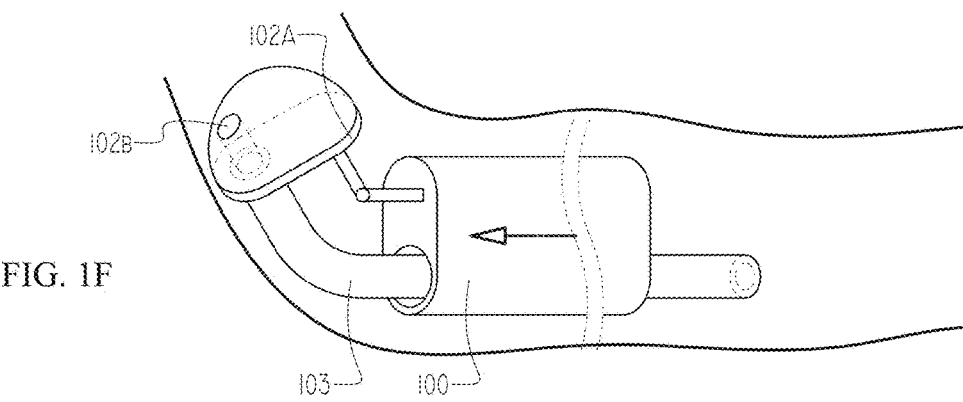
Figure 1G:
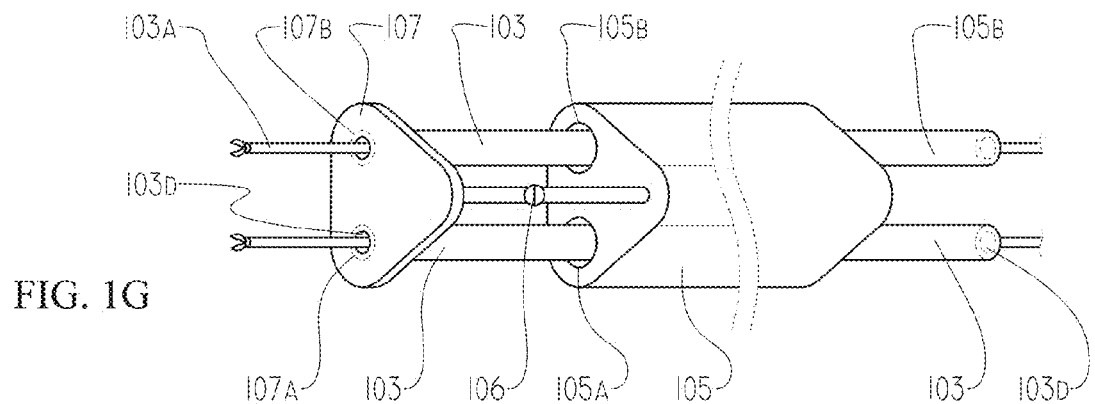
Figure 1H:
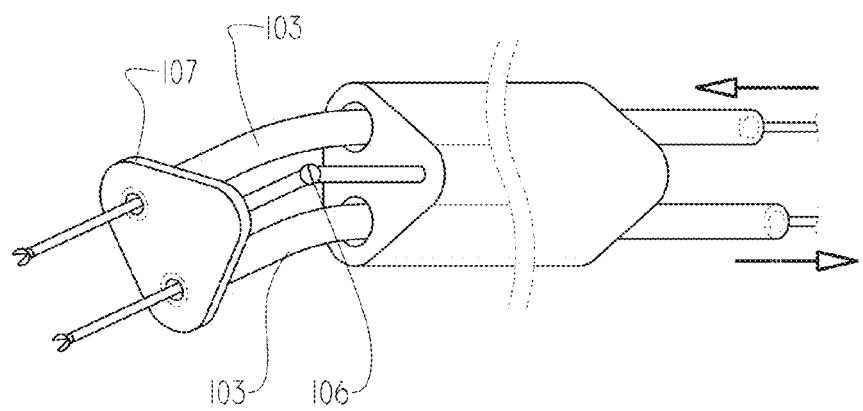
Figure 1I:
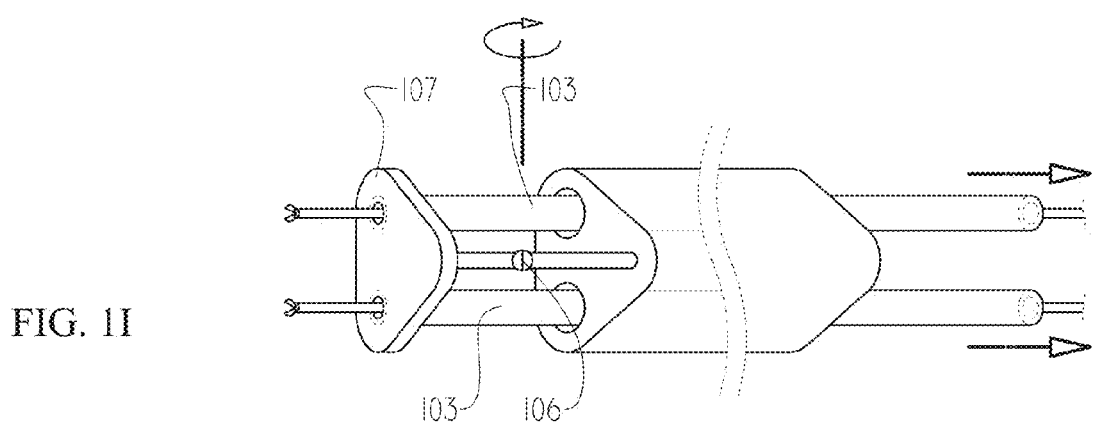
Figure 1J:
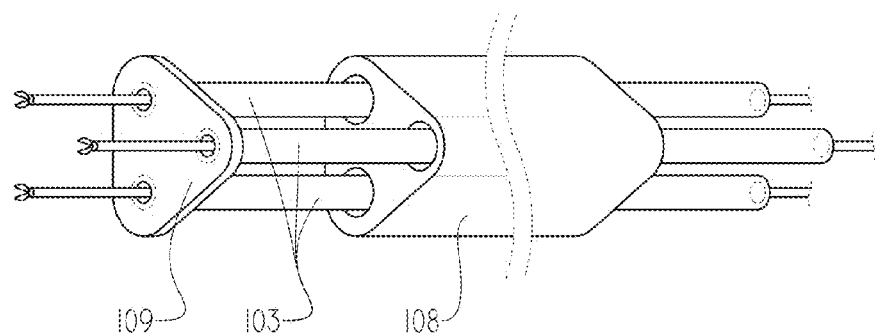
Figure 1K:
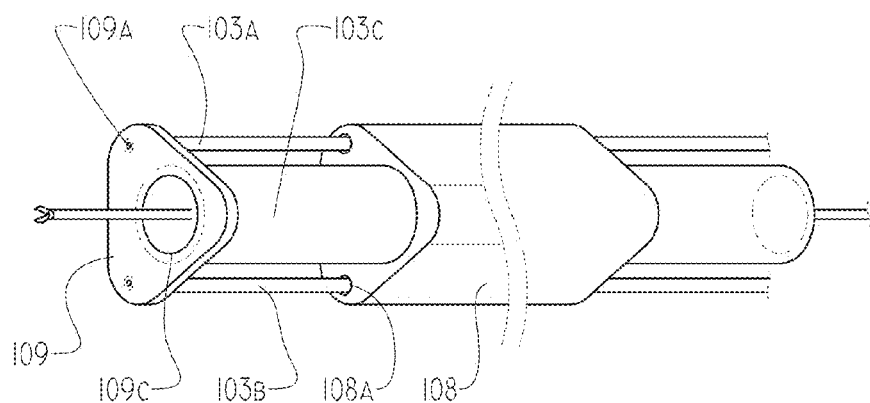
Figure 1L:
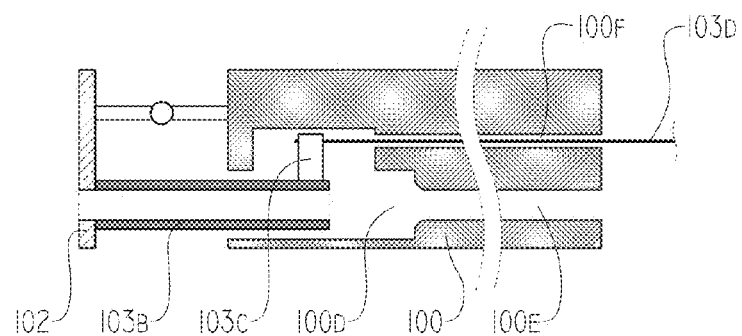
Figure 1M:
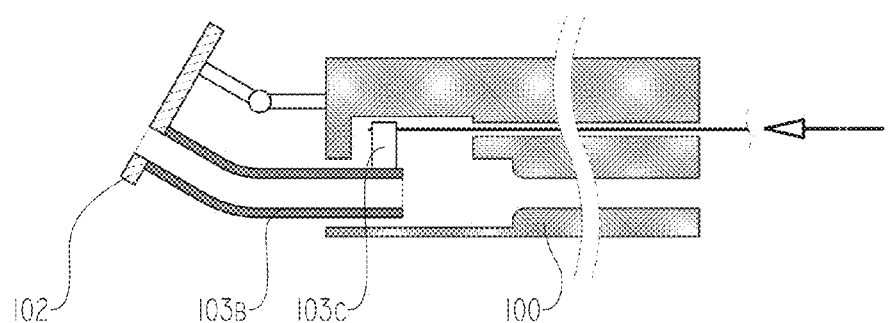
Figure 1N:
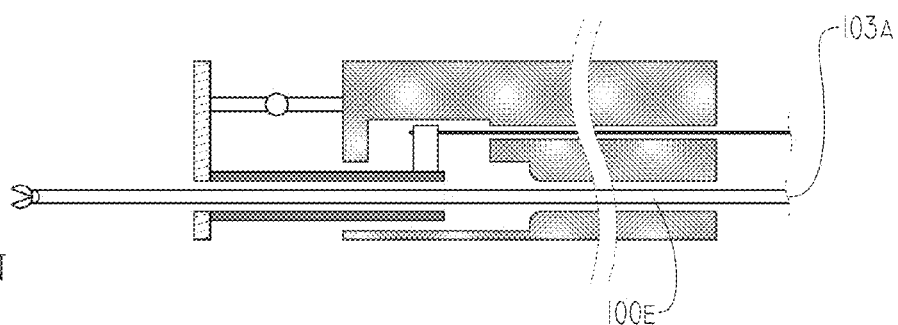

Referring now to the drawings, FIGS. 1A-1N are simplified schematics of embodiments of endoscopic steering systems, in accordance with some embodiments of the invention. These systems can be used inter alia to steer a cleaner (such as an intestinal cleaner) as described herein, but it is to be understood that their use is not limited to that exemplary context and that the steering systems here described can be used with general-purpose colonoscopies or other endoscopes, or with a catheter, or with other tools for use both within and without the body.

In the embodiments of FIGS. 1A-1N, a head section (e.g., 102) is coupled to a base section (e.g., 100) via a plurality of connector elements (e.g., 103, 101). When the relative length of these connector elements changes, the head changes its orientation. A particular feature of some embodiments of the invention, is that one of the connector elements (e.g., 103) is a tube with a lumen which may be used, for example, for liquid provision, for colon exhaust and/or for tool delivery. A particular feature of some embodiments of the invention is that one or more of the connector elements is flexible and elastic, while being stiff enough to be used for steering. However, if such steering aims the head at the colon wall (for example), the flexibility can come into play and allow the head to bend away from the colon and reduce or prevent injury thereto.

FIGS. 1A-1C illustrate a steering mechanism with one degree of freedom. The steering mechanism comprises a housing (100) and a head, such as a plate (102) connected by a connecting element include a joint (101), for example, a rotary joint or a living hinge. Housing (100) comprises a lumen (100a) wherein a pipe (103) can move axially. Optionally, pipe 103 is connected firmly (or integral with or otherwise mechanically coupled) to plate 102. In an exemplary embodiment of the invention, plate (102) comprises a hole (102a) coaxial with the pipe's bore. In some embodiments, a working tool of any kind (103A) could slide into the pipe and out from the plate's hole (102a). In some cases, this will not be done when pipe 103 is bent or during steering, as the tube stiffness may interfere with the bending/steering. But it may be done, especially if tool 103 has a flexible shaft. When the pipe slides forward, as shown in FIG. 1B, the plate rotates around the joint, reorienting the endoscope head. The working tool could then be freely moved as shown in FIG. 1C. Alternatively, the pipe can be used to move liquid or other materials into or out of the body. Optionally or alternatively, the tube can be used to pass fluids to a movement module. It is noted that the form of plate 102 shown in the Figure is not limiting, any form for "plate 102" can be used, even a sphere. Plate 102 is, for example, the base for the steered portion of the device. The features described with respect to this embodiment may be applied, with the appropriate changes to the other embodiments of the steering mechanism.

In some embodiments of the invention, pipe 103 can be twisted, thereby causing a rotation of the head.

As can be seen, in an exemplary embodiment of the invention, an endoscope steering mechanism is provided in which a same element serves both as a conduit and as a steering element. When a user pulls or pushes on a proximal portion of tube 103, movement is mechanically transmitted to the distal portion of tube 103 and to plate 102, as shown in the figures. The same tube 103 is hollow, and comprises a lumen 103E through which tools or materials can be transported. In an exemplary embodiment of the invention, pipe 103 has a diameter which is between 10% and 70% of the diameter of housing 100. In some embodiments, pipe 103 has a non-circular cross-section, for example, an oval cross-section or a triangular cross-section.

The mechanisms presented in FIGS. 1A-1N can be constructed, for example, from flexible pipe such as silicon, Tygon, Teflon or polyurethane. In an exemplary embodiment of the invention, in the resulting system, the pipes are able to transmit push/pull forces to plate 102, yet are sufficiently flexible that the steering mechanism allows for a degree of 'self-steering' or 'self-navigating' on the part of the endoscope head. In use, the angle of aim of an endoscope so controlled is directable by a user from outside the body, yet due to the soft and flexible properties of the pipe used that control is not rigid and the endoscope's head is able to yield to pressures imposed by, for example, contact with the sides of an intestine as the endoscope advances within the twisting intestinal lumen (or other body conduit lumen), as illustrated in FIGS. 1D-1F). Patient safety is potentially enhanced, since the risk of perforation or other damage to the body conduit is thereby reduced. In an exemplary embodiment of the invention, pipe 103 (or the mechanism in general, has a flexibility designed to provide a yielding of, for example, between 1 and 10 degrees per 100 grams. Optionally or alternatively, the yielding is, for example, between 1 and 10 degrees per 10 grams, per 1 gram, per 50 grams or intermediate amounts. The exact amount may be decided, for example, by a physician, based, for example, on patient characteristics and risk factors. Optionally, a range of yield properties are provided in different devices and a physician chooses between such devices, as desired. In an exemplary embodiment of the invention, the maximum deflection is between 20 and 80 degrees, for example, above 40 degrees.

FIGS. 1G-1I illustrate a steering mechanism with two degrees of freedom. The steering mechanism comprises a housing (105) and a plate (107) connected with a joint 106 having two degrees of freedom. For example, a Cardan joint, or U joint, or universal joint might be used. It should be noted that other joints may be used as well. Housing (105) defines two lumens (105A,105B) wherein a pipe (103) can move freely. Pipes 103 are connected firmly to plate 107. Plate (107) comprises holes 107A and 107B, which are optionally coaxial with the pipe's bore. A working tool of any kind (103A) could slide into each of pipes 103 and out of the respective hole (107A, 107B) in plate 107. In some exemplary embodiments of the invention, pipes 103 (in this and/or other embodiments) extend to outside of the body.

In one example of use, pushing one of pipes 103 forward within the body lumen while slightly retracting the other pipe 103 from the body lumen rotates plate 107 around joint 106 as illustrated in FIG. 1H. Pulling both pipes 103 rotates plate 107 in a plane orthogonal to that of the plane of rotation shown in FIG. 1H. Pushing on both pipes 103 would cause plate 107 to rotate out of the plane of the figure towards the reader. Pulling on those pipes would move it out of the plane of the drawing and away from the reader. It is noted that movements of pipes 103 is relative to the position of housing 105, which in some embodiments will constitute the main body of the endoscope.

In some embodiments, the pipes can only be used for pushing or for pulling. Additional reorientation direction may be provided by rotation of the endoscope as a whole.

FIG. 1J illustrates a steering mechanism with two degrees of freedom, in accordance with an exemplary embodiment of the invention. The steering mechanism comprises a housing (108) and a plate (109). Housing 108 comprises three lumens (optionally extending the length of the endoscope, cleaning system, or other steerable device) wherein 3 pipes 103 can move freely. Pipes 103 are firmly attached to plate 109. Plate 109 comprises three holes which may be positioned coaxial with the bore of pipes 103. As described above moving pipes 103 forward and backwards advances and retracts plate 109. Differentially moving some of pipes 103 more than others enables to control the angle and position of plate 109. Optionally, advancing of all the pipes or retracting thereof affects a stiffness of the head. Optionally, a skin (not shown) or other flexible casing (e.g., a pleated cover in the form of an accordion), in this and other embodiments, covers all or part of the volume bridging the head and the housing. In other embodiments, the pipes are selected to be soft enough to avoid damage to the body and such a skin is not used.

The joint could have one degree of freedom like a hinge, or two degrees of freedom like a Cardan joint, or three degrees of freedom like a the human hip joint, allowing movement forward and backwards, to the left and right sides, and rotation around a central axis.

In an exemplary embodiment of the invention, the mechanisms shown herein are adapted for being mounted at the end of an existing endoscope or other intrabody tube, optionally, with pipe 103 passing through a lumen of the endoscope and housing 108 being mounted on a forward end of the endoscope.

Optionally, the lumens of one or more pipes are used to pass wires for a light and/or imager which is optionally provided in the steered element.

FIG. 1K illustrates a steering mechanism with two degree of freedom, where the large bore pipe (103C) is of limited length and is connected firmly both to the endoscope's body (108) from one side, and to the plate (109) from the other side, replacing the joint shown in FIGS. 10A-10J with flexible pipe. Large-bore pipe (103C) can be the matter exhaust conduit, yet also be part of the steering mechanism.

FIGS. 1L-1N illustrate a steering mechanism with one degree of freedom. This steering mechanism comprises a distal pipe 103B and a medial cable 103D. The housing (100) comprises a lumen (100D) wherein a pipe (103B) can move freely forward and backward. An additional smaller lumen (100E) is formed within housing 100 and can be continued the length of the endoscope. The axis of lumen 100E is aligned with the proximal portion of pipe 103B, so a working tool (103A) can move freely through both lumen 100E and lumen 100D, and into the proximal portion of flexible pipe (103B). The short pipe (103B) is connected via a block (103C) to cable (103D), which may be, for example, a metal cable.

Steering cable 103D may be long (e.g. 1-2 meters) and may optionally be fabricated from metal cable, or any other type of cable with high strength and low friction with respect to a containing lumen (or the lumen may be appropriately coated). In use, the short flexible pipe (103B) enables to steer the endoscope through the turns and twists of the body conduit in which it is inserted, while only cables need to be manipulated over most of the length of the endoscope and/or in a handheld steering mechanism.

The combination of pipe 103B and cable 103D can also be implemented in conjunction with the embodiments shown in FIGS. 1A-1K, with one, some, or all of the flexible hollow pipes receiving push and pull forces from a cable as shown in FIGS. 1L-1N.

Combination Endoscope and Exhaust/Cleaning System

Figure 2:
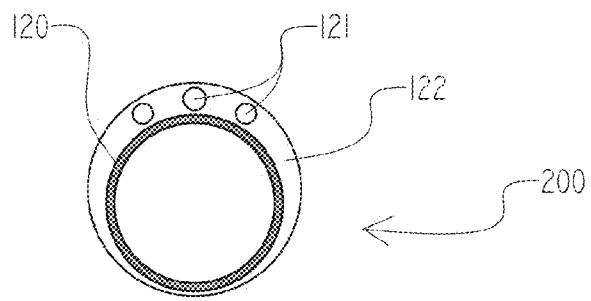
FIG. 2 is a simplified schematic of an embodiment comprising a cleaning system for cleaning a body cavity, according to some embodiments of the present invention.

As noted herein, a cleaning system is optionally integrated with an endoscope or colonoscope. Attention is now drawn to FIG. 2 which is a simplified schematic cross-section of an embodiment according to the present invention, which embodiment comprises a cleaning system for cleaning a body cavity such as for example a lower GI tract. FIG. 2 shows a cleaner 200 which comprises a housing 122, one or more irrigation channels 121 for providing a liquid which may optionally be injected into the body cavity under pressure, and an exhaust pipe 120. This pipe optionally houses a cleaning and/or shredding mechanism, for example, as described below. FIG. 2 is optionally a stand-alone system operable to clean an intestine without requiring an optical unit and without being part of an endoscope.

Figure 3A:
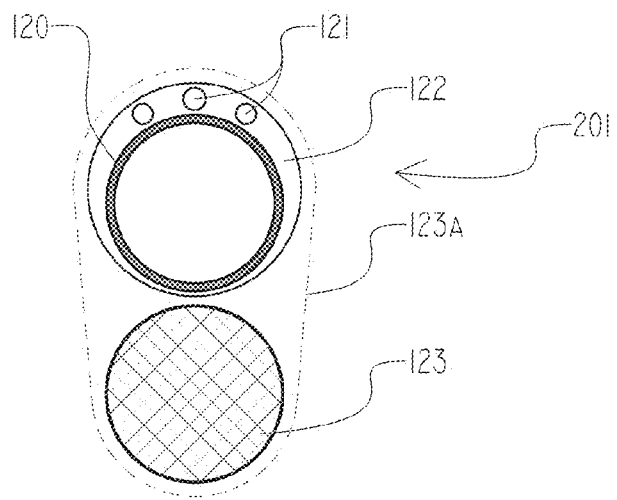
FIG. 3A is a simplified schematic of an embodiment comprising a cleaning system combined with an endoscope, according to some embodiments of the present invention.

FIG. 3A presents a system 201 according to an embodiment of the present invention in which a cleaning module similar to that shown in FIG. 2 is integrated with an endoscope. Cleaning elements 120, 121, 122 as defined above are integrated with an optics system 123 to provide an endoscope with cleaning capabilities. Alternatively, instead of being manufactured as a unit, system 201 can be presented in a form wherein the cleaning portion (120, 121, 122) is constructed separate from optics portion 123, and one or more connectors or attachments are provided for attaching the cleaning portion to the optics portion. One example of such an attachment is a hollow tube which is placed over the endoscope and the cleaning system. In another example, the cleaning system include an axial hollow for receiving the endoscope.

Figure 3B:
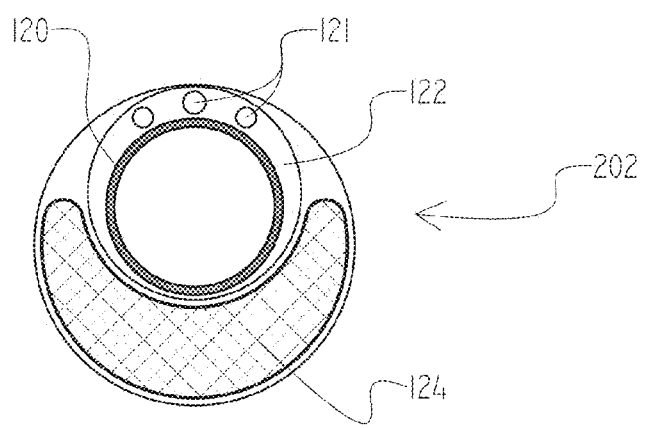
FIG. 3B is a simplified schematic of an embodiment comprising a cleaning system combined with a locomotor system, according to embodiments of the present invention.

FIG. 3B schematically presents a system 202, in accordance with some embodiments of the invention in which a cleaning module similar to that shown in FIG. 2 is integrated with a locomotor system 124 operable to advance system 202 within a body conduit such as a bowel. U.S. Patent Application US20080103360, which is incorporated herein by reference, provides examples of such locomotor systems. Other systems may be used as well. In FIG. 3B a cleaning module (120, 121, 122) is integrated with a locomotion/navigation system here generally labeled 124.

In some embodiments, the locomotion system has a relatively large-diameter head section and a relatively small diameter cable and tubing section. Optionally, the cleaning section is attached so that it cleans sections in front of, in the middle of and/or in the back of the locomotion section head. Optionally, the cleaning mechanism is aimed to a side of the colon opposite the motion mechanism, for non-axial motion mechanisms. For example, the head may be mounted axially in front of the cleaning system. An exemplary locomotion system is presented in FIGS. 3H-A through 3J and discussed below. As with the system of FIG. 3A, the cleaning element and the locomotion element can be manufactured together as a unit, or manufactured separated with an attaching arrangement (not shown in the Figure) provided to enable the elements to be attached to one another and used together.

Figure 3C:
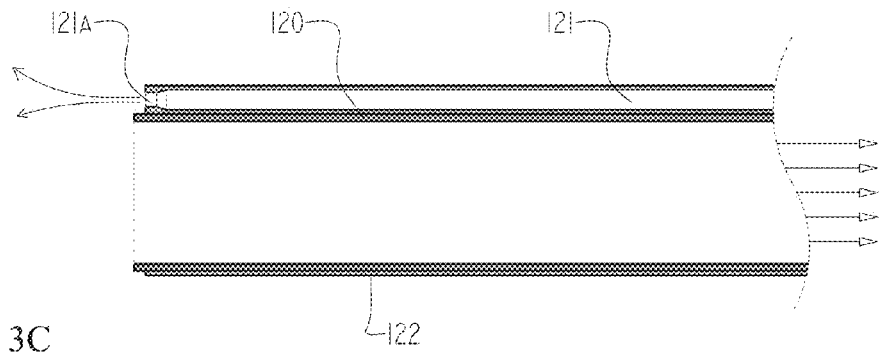
FIG. 3C is a longitudinal cross-section of the embodiment shown in FIG. 2, according to some embodiments of the present invention.
Figure 3D:
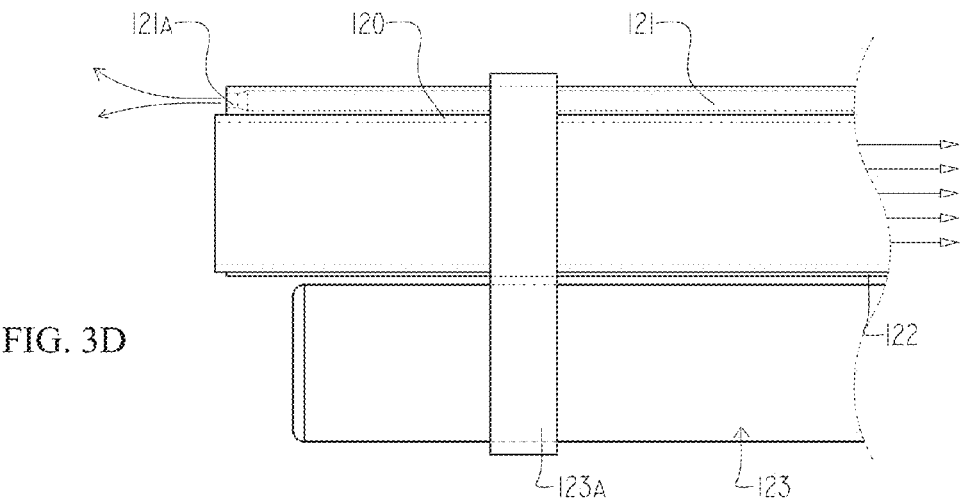
FIG. 3D is a side view of the embodiment of FIG. 3A, according to some embodiments of the present invention.
Figure 3E:
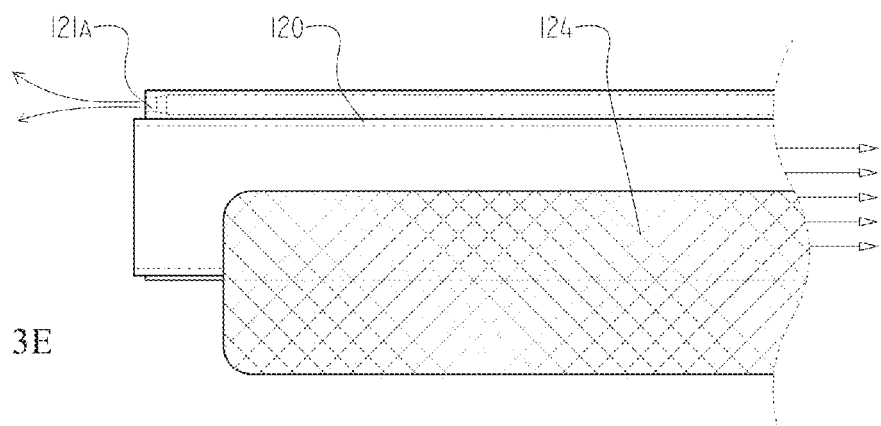
FIG. 3E is a side view of the embodiment of FIG. 3B, according to some embodiments of the present invention.

FIG. 3C is a side cross section of FIG. 2, FIG. 3D is a side cross-section view of FIG. 3A, and FIG. 3E is a side view of FIG. 3B, in accordance with exemplary embodiments of the invention, showing more details of integration of a cleaning system with an endoscope/colonoscope.

Figure 3F:
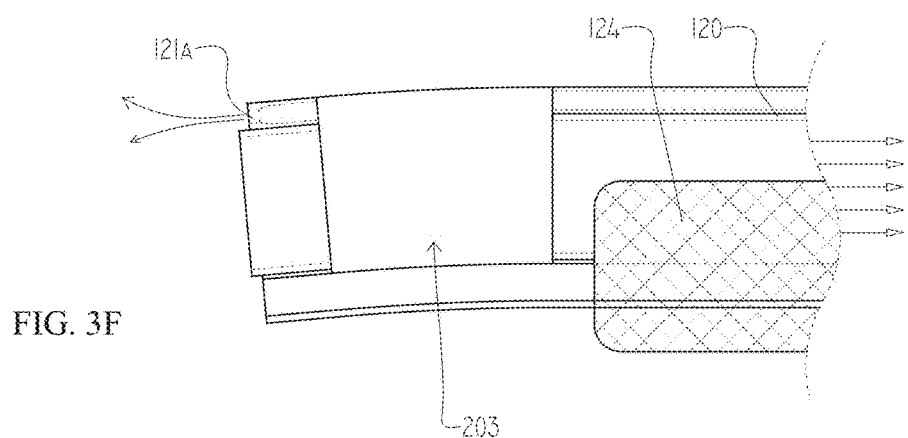
FIGS. 3F-3G illustrate a side view of an endoscope with cleansing capabilities and a self-propelling device, and having a steerable segment at the distal end, according to some embodiments of the present invention.
Figure 3G:
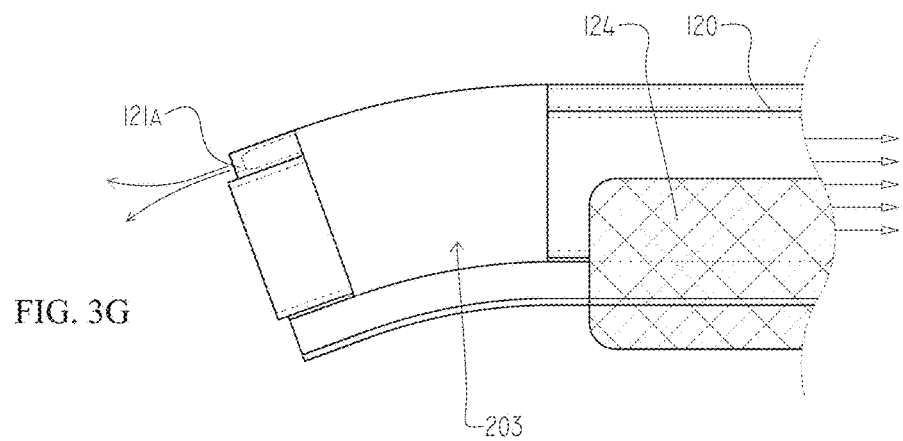

FIGS. 3F-3G illustrate a side view of an endoscope with cleansing capabilities and self-propelled device (124), and having a steerable segment (203) (e.g., as described above, optionally using the exhaust conduit as one of pipes 103 and/or using the endoscope as one of the rods/cables) at the distal end thereof.

Figure 3I:
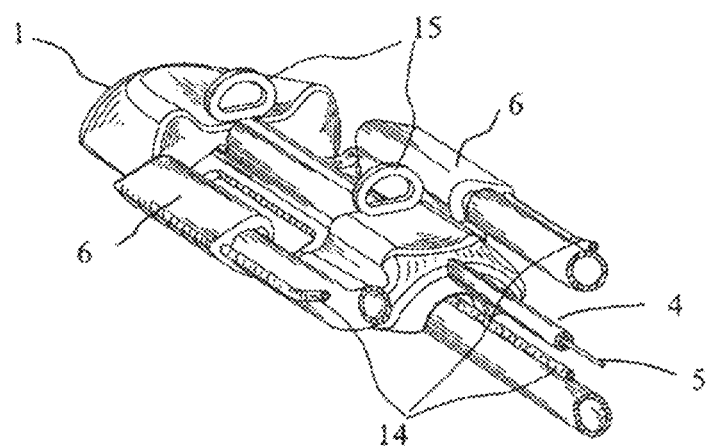
Figure 3J:
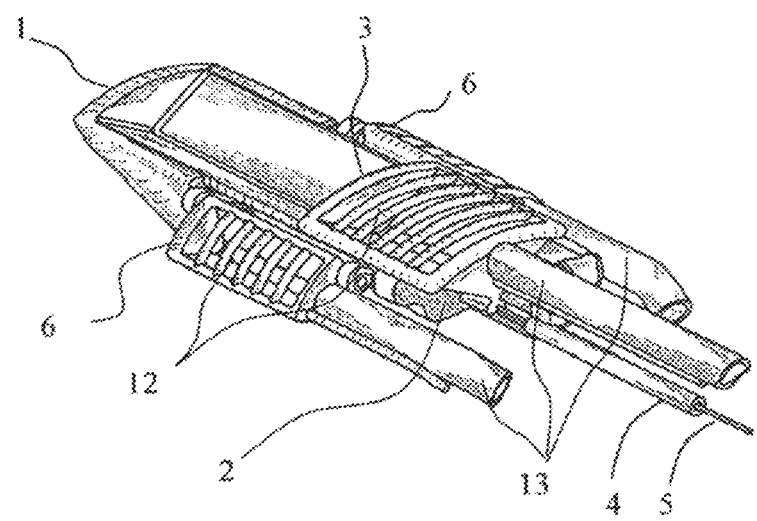

FIGS. 3H-3J present an exemplary locomotion system for use with any of the embodiments presented herein.

FIGS. 3H-A to 3H-H illustrate the cycle of a self-propelled device. The device comprises one or more moveable attachment element ("MAE"). MAE 19 slides in a linear manner within slider 19A incorporated into the endoscope body Immovable Attachment elements ("IMAE") 18 are connected to slider 19a in such a manner that they can move sideways but not forward or backwards.

FIGS. 3H-A to 3H-C show forward movement of the MAE while the endoscope body as a whole does not move.

FIGS. 3H-D to 3H-E show MAE 19 connected by vacuum to the lumen wall, while pressers 18A disconnect IMAE 18 from the lumen wall.

FIGS. 3H-F to 3H-G shows the actual forward movement of the endoscope body.

FIGS. 3H-H represents the last step in the cycle, enabling the self-locomotion endoscope to start the cycle from the beginning.

FIGS. 3I illustrates the device of FIGS. 12H as seen from above. An endoscope comprises endoscope body 1 and two IMAE 6 connected in a slider joint—that enables sideways movement only. Rings 15 are provided so that a pipe of a set diameter could be inserted as a working channel or a cleansing pipe and/or as a whole cleaning system, such as described herein.

The MAE (not shown in this Figure is optionally driven by a cable 5 enfolded in a cable jacket 4).

FIG. 3J illustrates a view from below of the device, showing endoscope body 1), MAE 3 moving on a slide 2), and supply pipes for the MAE and IMAE 13). The MAE and IMAE comprises housing 3,6 covered with fins 12 that keep the tissue from clogging the attachment element.

Reduced Blockage

Figure 4A:
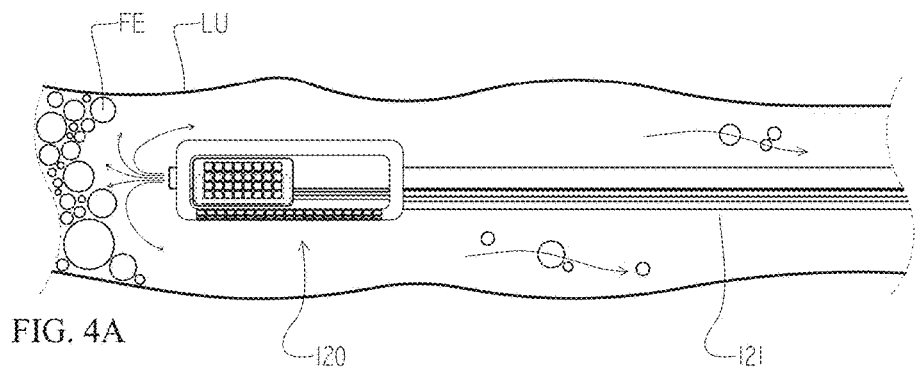
FIGS. 4A AND 4B present cleaning devices.
Figure 4B:
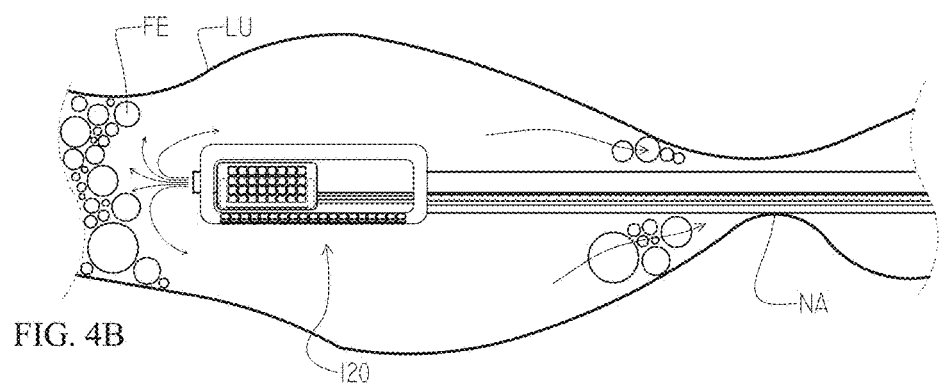
Figure 4C:
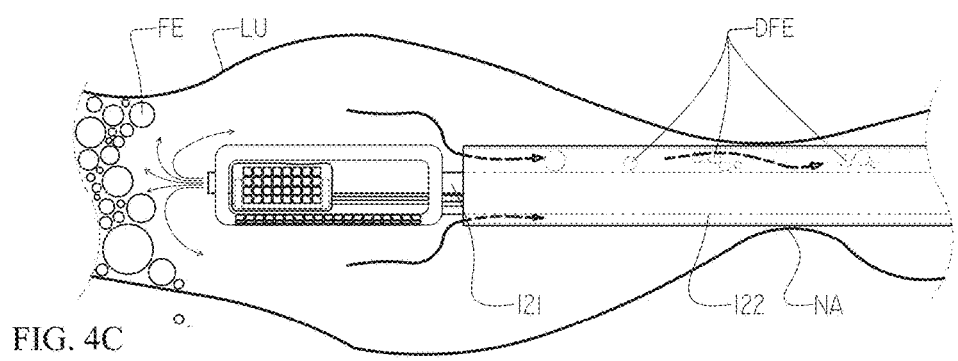
FIGS. 4C-4E present cleaning devices which ensure an open exhaust passageway, according to some embodiments of the present invention.
Figure 4D:
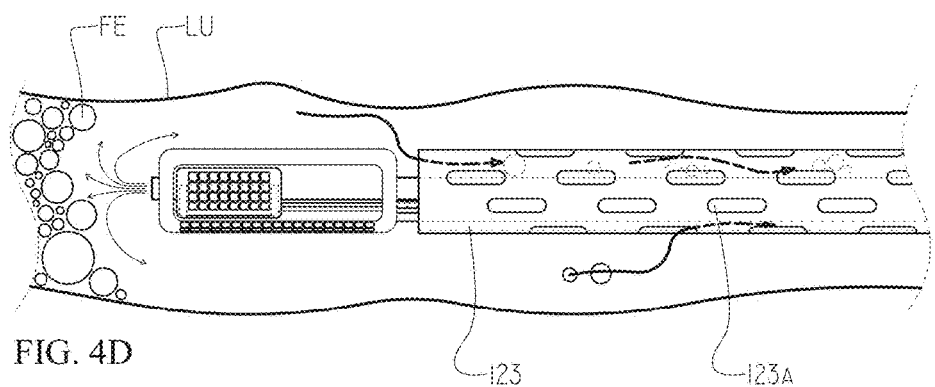
Figure 4E:
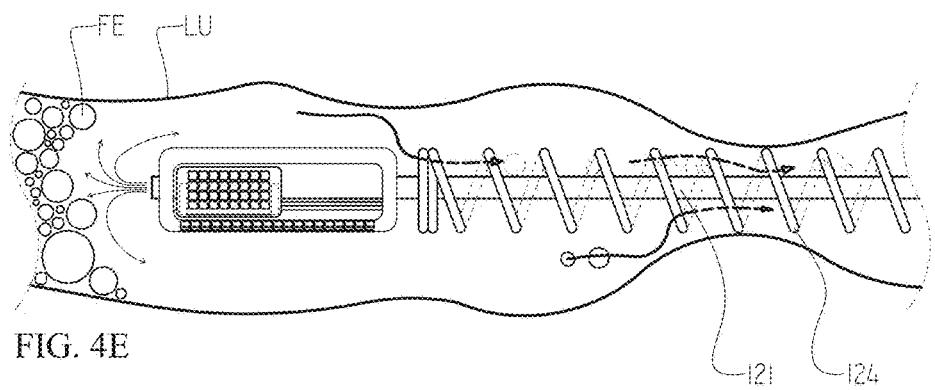

FIGS. 4A-4B present side views of embodiments of cleansing system for cleansing a body cavity, with a potential blockage issue, and FIG. 4C-4E present side views of embodiments of cleansing systems according to embodiments of the present invention, potentially with a reduced blockage issue. Designs presented in FIGS. 4C-4E are useful for cleaning the lower GI tract, but as stated elsewhere in this document, the claimed embodiments are not limited to that exemplary context.

FIG. 4A presents a system in which liquid, optionally under pressure, is introduced into intestine, where it mixes with fecal matter. The fecal matter is partially dissolved in the liquid and partially carried away by the liquid flow, and exits the body through the colon and rectum. FIG. 4B shows a potential disadvantage of this system, where exhausting of the liquid and fecal matter from the body is impeded by lateral compression of the intestine, e.g. by movement of the lumen, peristaltic movements, pressures from tumors, fat, other organs, or any other source.

In an exemplary embodiment of the invention, an outer tube which is resistant to such compression is provided, for such exhaust. Optionally, such a tube is provided around a liquid providing tube of an existing system. Optionally or alternatively, a same tube is used for inserting water and exhausting the intestines.

In an exemplary embodiment of the invention, the tube is attached at its distal end to a self-propelling mechanisms and/or a steering mechanism. Optionally, an opening in the side of the tube is provided for ingress of dissolved and semi-dissolved fecal matter.

FIG. 4C presents an embodiment according to the present invention whereby an evacuation tube 123, which is resistant to such compression, is provided to facilitate evacuation of the liquid and fecal matter. In an exemplary embodiment of the invention, the tube includes a plurality of ring-shaped stiffening elements along its length. Bending of the tube is optionally not significantly impeded by the rings. Optionally, the ring segments are spaced, for example, between 1 and 40 mm apart, for example, between 3 and 20 mm apart. Optionally or alternatively, a spiral element which resists compression is provided therein, with optionally similar pitches.

FIG. 4D presents an embodiment according to the present invention, wherein an evacuation tube 123 comprises multiple input orifices 123A through which fecal matter loose within the intestine and/or loosened by an irrigating liquid can pass into exhaust passage 123. A plurality of openings 123A helps prevent clogging by providing multiple entrances to exhaust passage 123. It is noted that tube 123 can optionally be used to input water to the body if desired, (e.g., to clear such blockages and/or for other uses) by supplying water under some pressure at a proximal end of passage 123. As described below, precautions may be taken to avoid over-pressurizing the colon and to avoid filling the colon with excessive amounts of water. In an exemplary embodiment of the invention, the apertures form at least 10%, 30%, 50%, 60% or intermediate percentages of the surface area of the last 10 cm or 5 cm of the distal end of tube 123. A larger percentage of free space is shown by the coil of FIG. 4E, which can have a free space of 70%, 80%, 90% or more.

FIG. 4E presents a side of an alternative construction for enabling free flow of liquid and solid matter out of the intestine: a spacer 124, optionally formed as a spiral coil or spring, is provided. Coil 124 prevents the intestinal wall from collapsing towards the device and cutting off the exhaust path for solids and liquids, since spacer 124 provides at least a minimum diameter of exhaust passageway which will not be closed by pressures which would reduce or eliminate the exhaust path as shown in FIG. 4B. In an exemplary embodiment of the invention, such a coil is inserted using an over tube, which overtube is retracted, while leaving the coil in place. Optionally, a tube with only its distal end formed as a coil is used, or most of the coil remains covered by the tube. For example, the exposed coil section can be, for example, between 5 and 20 cm long.

Exemplary Evacuation and/or Shredding Mechanism

Attention is now drawn to FIGS. 5A-5D which are simplified schematics presenting a cleaner 130 with an exhausting and/or morselizing mechanism according to some embodiments of the present invention. In an exemplary embodiment of the invention, this mechanism comprises a spring of fixed or varying diameter, which, as rotated, can breakdown fecal matter and/or assist in conveying fecal matter to outside of the body.

Cleaner 130 is optionally combined with an endoscope and/or with a locomotion system, having a large bore working channel 131 which comprises a feces mover, such as a helical spring or coil 132 or a screw used to move feces from the endoscope's distal tip to a proximal collection station outside the body. Helical spring 132 is caused to rotate by an external or internal motor (not shown in the figure). Rotation of spring 132 in an appropriate direction will cause solid components of the feces/liquid mixture to be transported from distal to proximal portions of the device, and out of the body. Optionally, spring 132 can be provided with an additional motor or actuator which axially slides part or all (e.g., depending on whether the distal end is at least somewhat freely movable or axially fixed) of spring 132 backwards and forwards within the conduit, e.g. as an additional method for moving solid matter caught up in the windings of the spring out of the body and/or for assisting in breaking down feces.

Optionally, the inner surface of channel 131 includes one or more protrusions which hold the coil in place and/or help in breaking down feces.

In an exemplary embodiment of the invention, spring or coil 132 have a pitch of between 1 mm and 30 mm, for example, between 5 and 20 mm. Optionally, the diameter of spring 132 is less than the inner diameter of lumen 131 by, for example, 0.1-10 mm, for example, 1-3 mm Optionally, the cross-section of the coil is flat, rather than rounded as shown. Optionally, the coil has a non-smooth inner surface, for example, including protrusions thereon. Optionally, the spacing are selected so that fecal matter can be crushed between the coil and the lumen wall and/or within the lumen, while allowing larger pieces of fecal matter to pass without clogging.

Figure 5A:
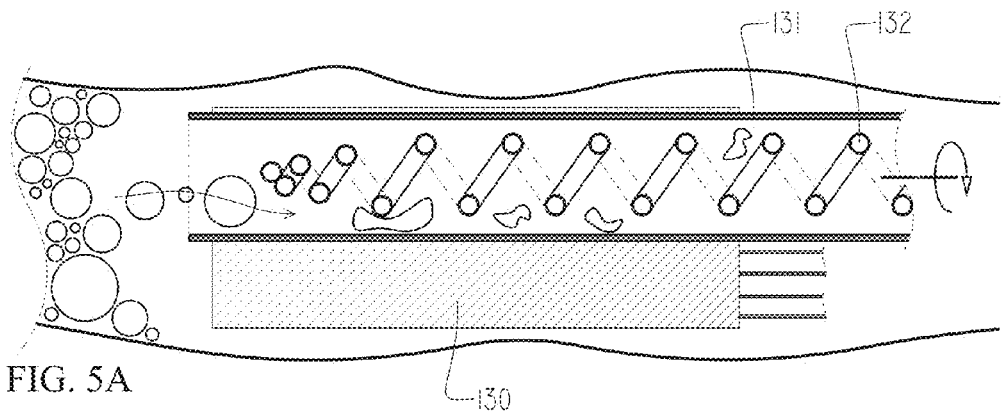
FIGS. 5A-5D present cleaning devices which comprise matter transportation systems and matter shredding systems, according to some embodiments of the present invention.
Figure 5B:
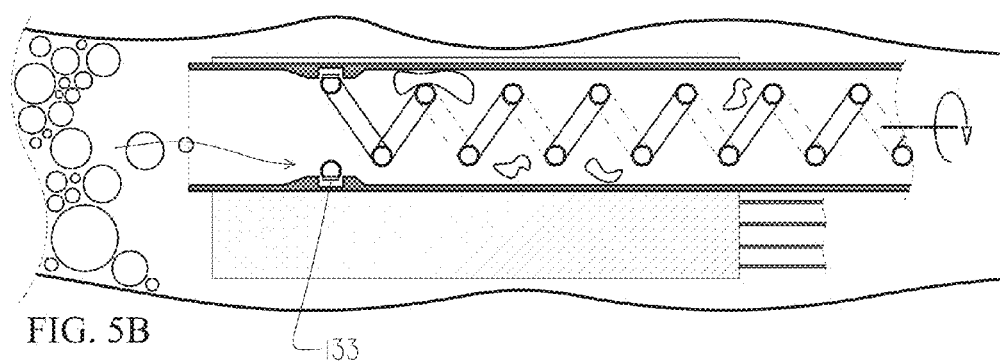

FIG. 5B is similar to FIG. 5A, with the addition of a rotary sliding connection 133, such as a bearing 133 which holds spring 132 (or a circular end thereof) in place and allows it to rotate while preventing it from moving forward or backwards within the device. Optionally, the width of bearing 133 is set to allow some axial motion. Optionally, only (or an additional) distal stop is provided. Optionally, such a distal stop serves to preventing coil 132 from moving beyond the device's distal end and into contact with body tissues.

Figure 5C:
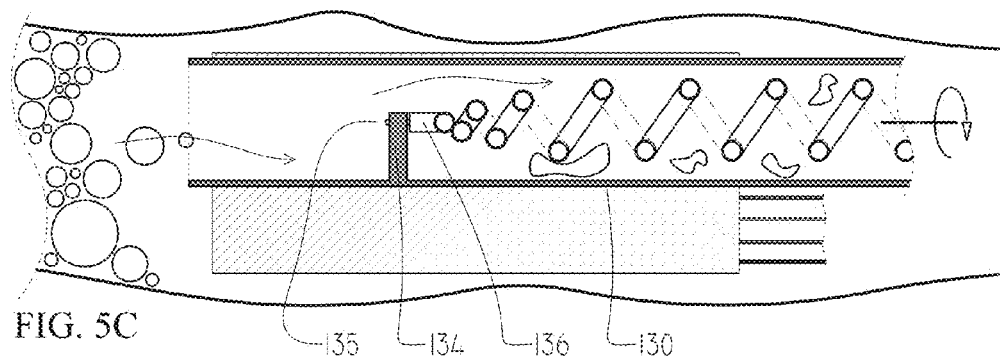

FIG. 5C illustrates an alternative design in which a spring tip 136 is connected to a rotary hinge 135 which holds spring 132 in place, allowing it to rotate while preventing it from moving forward or backwards within the device. Optionally, hinge 135 is connected to an arm 134 that connects to the device housing.

Figure 5D:
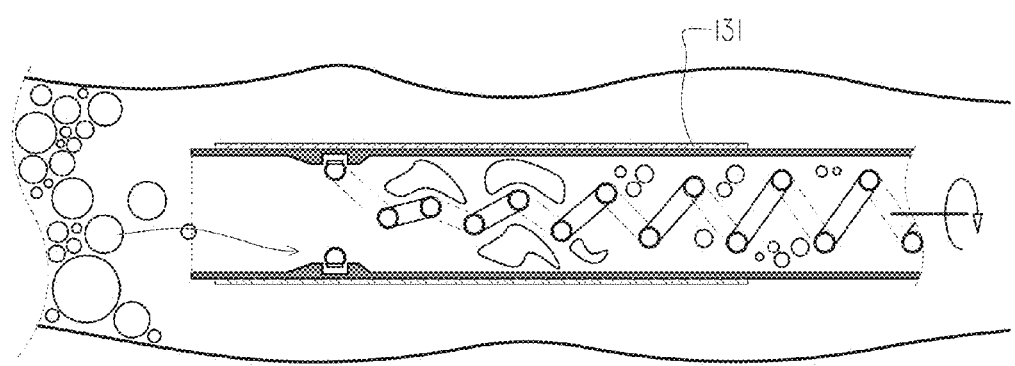

FIG. 5D is a simplified schematic of a cleaning device in which a single lumen serves both as a liquid injection conduit and an evacuation conduit. In some embodiments liquid is injected or otherwise provided into the body through the large-bore lumen of the device (optionally using a tube temporarily inserted into the lumen to the colon), and then an optional matter transportation device (which could be any device presented herein, or any other matter transporting device) facilitates evacuation of matter. Optionally or alternatively, water insertion and evacuation proceed in pulses, optionally alternating, optionally controlled by external circuitry.

In an exemplary embodiment of the invention, the evacuation mechanism shreds fecal matter. Optionally, the spacing between coils is selected so that unshredded fecal matter will pass through the central lumen of sprint 132. In an exemplary embodiment of the invention, the distance between coils starts larger and then becomes progressively smaller so as to prevent large fecal matter form existing the lumen of the coil. In an exemplary embodiment of the invention, the diameter of the coil increases along the length of the coil, such that large fecal matter can, initially fit between the coil and the lumen wall, but if not broken down, will migrate into the coil. The changes in spacing between the coils and the changes in diameter may be coordinated according to properties of the fecal matter, for example as selected by the physician.

In an exemplary embodiment of the invention, a shredding section of the coil is between 2 and 20 cm long, for example, between 3 and 7 cm long. Optionally, over such a section, the spacing between coils goes down by between 20% and 90%, for example, 50%, or more. Optionally or alternatively, over such a section the diameter of the coils can increase by a factor of, for example, between 2 and 6. In an exemplary embodiment of the invention, the initial diameter and spacing between coils is 3 mm and 10 mm respectively. In some embodiments, the initial spacing between coils is small and then grows and then optionally decreases. In an exemplary embodiment of the invention, the speed of rotation of the coil is between 1 and 7000 rotations per minute, for example, between 3000 and 5000, or more, optionally controllable by an external circuit and user input and/or be set by a manual rotation speed.

Alternative Evacuation Mechanism

Figure 6A:
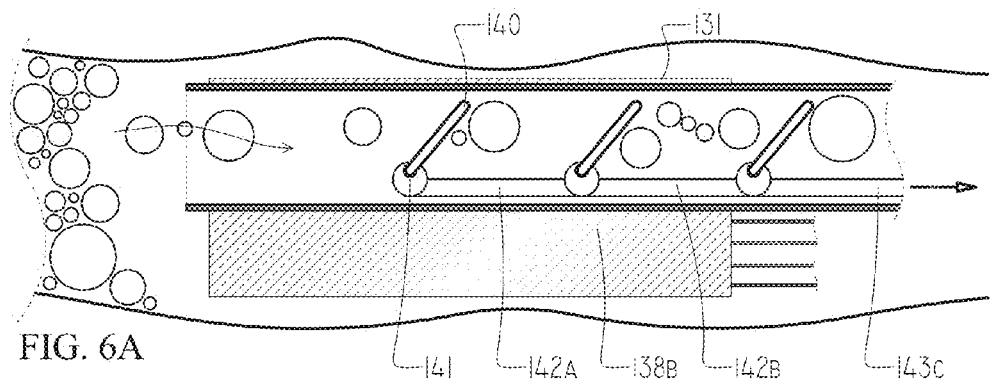
FIGS. 6A-C present cleaning devices which comprise a mechanism having moveable flaps, for transporting materials out of the body according to some embodiments of the present invention.
Figure 6B:
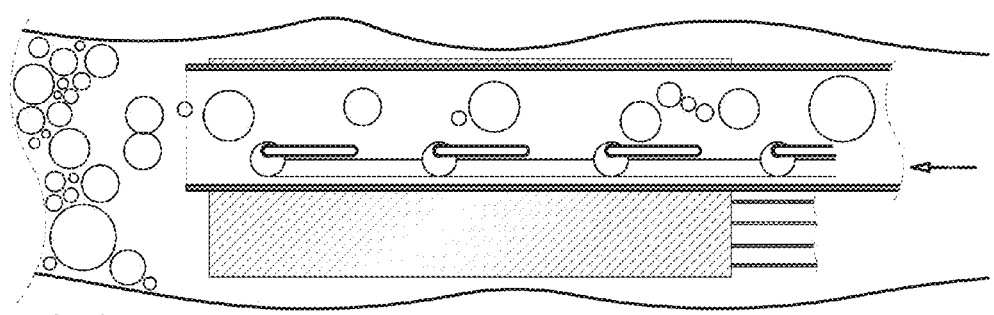
Figure 6C:
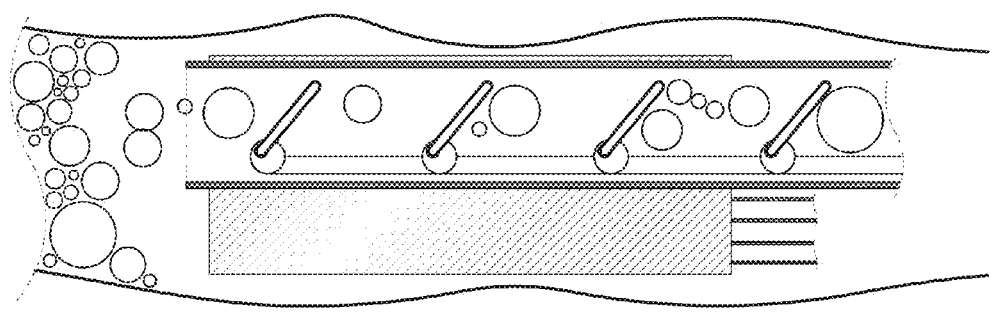

FIGS. 6A-6C are simplified schematics illustrating a cleaning system according to an embodiment of the present invention. FIGS. 6A-6C show a cleaning system optionally embodied with an endoscope, and optionally comprising a locomotion module. In this system, exhausting of an exhaust lumen is optionally provided using reciprocated motion and vanes (or flaps). When the vanes are closed, they are retracted out of the body, pulling fecal matter with them.

In the embodiment shown, exhaust passageway 131 comprises one or more flaps 140 connected to spring loaded joints 141. Each joint is connected to a driving rod, which rods are labeled 142A-C in the figure. This combination produces a one-way exhaust transportation system which operates in a cycle. This can be described as a 4 stroke system: a) close flaps (so lumen is free), b) move rods and flaps forward towards the distal end of the device (FIG. 6B), c) open flaps, d) move rods and flaps towards the proximal end of the device, thereby moving materials away from the body.

The driving rods can be moved (e.g. by an external motor) in a linear or in a rotary direction. In an alternative embodiment, manual motion is provided.

In an exemplary embodiment of the invention, the flaps close due to the resistance of the fluid in the lumen against which they are pushed. The flaps then open due to the spring loading (optional) or due to being pulled against fecal matter. In an exemplary embodiment of the invention, the flaps, when open, substantially seal lumen 131. In an alternative embodiment the flaps fill only less than 90%, 80%, 70%, 50% or intermediate percentages of the cross-section of lumen 131, when open.

In an exemplary embodiment of the invention, as shown, the driving rod is located near the wall of the lumen, so as to provide a greater lumen cross-section. Op the flaps are flexible and will bend, rather than break, if caught against a piece of fecal matter. Optionally or alternatively, one or more of the flaps is provided as a plurality of fingers. In an exemplary embodiment of the invention, the flaps are formed as a rubber membrane with a flexible metal edge. Optionally, the edge connects to the (one or more) driving rod to form a spring-loaded connection, the tension being provided by twisting of the metal edge.

Exemplary System and Optional Envelope

Figure 7A:
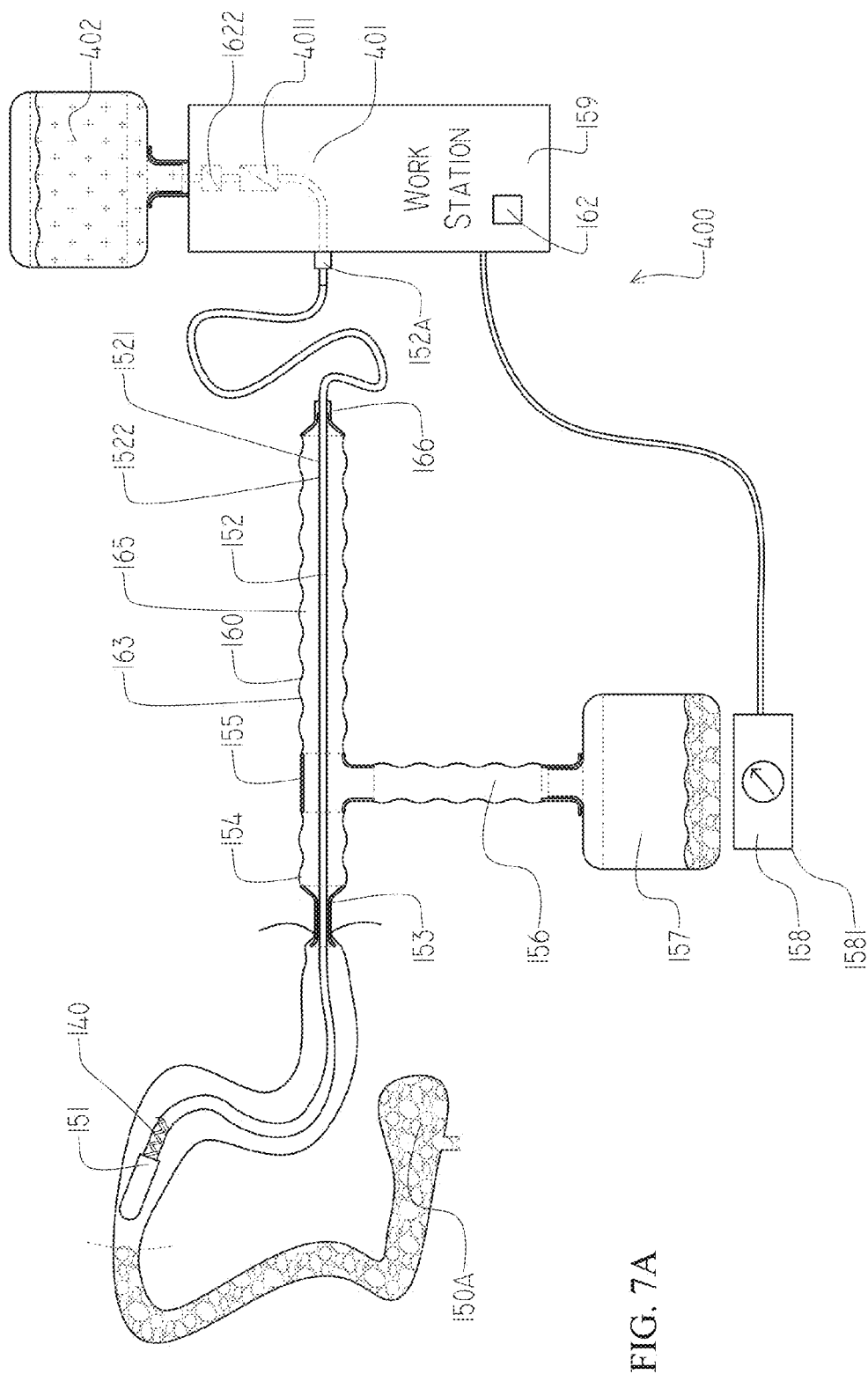
FIGS. 7A-C present devices for cleaning an intestine with capture and measurement of material removed from the body according to some embodiments of the present invention.
Figures 7B, 7C:
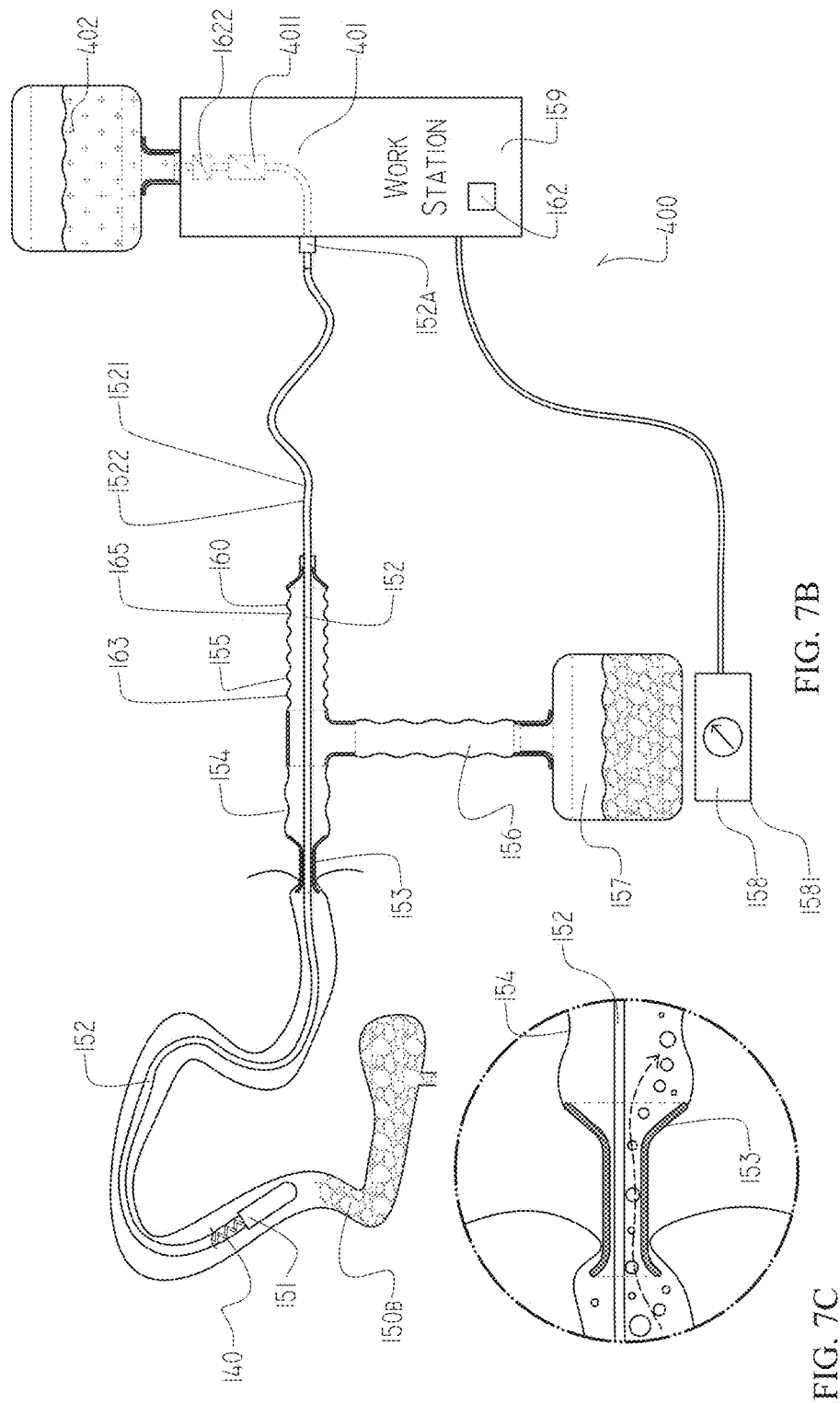

FIGS. 7A-7C are simplified schematics illustrating an cleaning system 400 according to an embodiment of the present invention, illustrating several potentially useful features which may be used in combination with the above features or as part of a different cleaning system. In particular, these figures show methods for containing the exhausted fecal material and safety features for reducing potential of damage to the GI tract. In an exemplary embodiment of the invention, a kit is provided which is used once and then disposed of with the fecal matter exhausted from the body.

The human colon is filled with approximately 2 liters of feces. To clean the feces, water or other liquid is introduced, and the outcome is feces combined with water. In an exemplary embodiment of the invention, it is made possible and/or convenient to keep track of how much water is inserted and how much water and feces is exhausted from the system. Thereafter, it is possible to keep track and balance these quantities and thereby to avoid over-distending the colon, which would endanger the patient.

In an exemplary embodiment of the invention, a closed system is provided. Such a system can both assist in keeping track and also assist in hygienic and/or convenient disposal of feces. It should be noted that it is also envisioned to provide only one of these features.

System 400 comprises a cleaning head 151 insertable in a colon and positioned at the distal end of a pipe 152 whose proximal end is connectable, through a connector 152A, to a water source or tank 402. Pipe 152 is optionally incorporated in an endoscope 1521 or other tool 1522 which comprises cleaning head 151 at a distal end. System 400 also optionally comprises an exhaust matter collection apparatus 165, and optionally comprises an exhaust matter transportation apparatus 140 (e.g. a rotatable helix within pipe 152). Optionally or alternatively, an envelope 160 is provided which encloses pipe 152 and also seals to the anus, so that all exhausted fecal matter remains in the envelope. Optionally, the envelope is sold as a kit, optionally with other tubes or components as part of the cleaning system.

System 400 uses a water input measuring apparatus 401 such as a flow gage 4011 (or measuring, for example, pressure in tank 402 to determine volume left in tank 402) which may be positioned anywhere between water source 402 and cleaning head 151. Optionally, the height of tank 402 is used to control the pressure of water flow into the colon and/or the final pressure in the colon. Optionally or alternatively, a pump is used to advance water from source 402 into the colon. Such a pump is optionally also operable in a reverse direction and/or used as a valve, to stop flow. An exemplary placement for flow gage is shown FIG. 17A, where gage 401 is positioned between water source 402 and pipe/endoscope 152's connector 152A which connects to water source 401.

Evaluating how much feces and water exists the system is difficult due to the discontinuity of the material, which can include feces, water, air, lubricants and other sorts of matter. System 400 solves this problem by providing a scale 158 for weighing feces, water, and any other materials that exit the body during cleaning. Optionally, scale 158 is integrated with envelope 160. Alternatively to a scale, the envelope includes a vertical container and the pressure at the bottom of the container (e.g., measured using a pressure sensor) indicates its filling height with liquid (feces having a density similar to that of water).

In the embodiment shown, a T-junction 155 is used, whereby feces exit the body, reach the T-junction and fall into the container, enter envelope 160, drop into the vertical portion of T junction 155, and fall through a sleeve 156 into a collection container 157. Optionally, container 157 has a volume of between 2 and 20 liters, though other volumes may be provided as well. Tank 402 may also have similar volumes. Optionally, container 157 is made of a flexible material, optionally strengthened (e.g., using a web) to not tear under the weight. Optionally, container 157 has a wheeled bottom.

In the exemplary embodiment shown in the figure, a working station 159 supplies clean water from a reservoir 402. Optionally, flow from supply 402 may be controlled by a controller 162 controlling a valve 1622. Optionally, control is applied to reduce flow when pressure (e.g., as sensed using a pressure sensor in fluid communication with the colon) is high or when the scale indicates exhausting is not fast enough.

Clean water travels through flow gage 401, through connector 152A and into pipe 152 and to a cleaning head 151. Pipe 152 is insertable through a speculum 153 into to the body's lumen, as seen in FIG. 7C. Water supplied through pipe 152 washes the dissolved or partially dissolved feces out of the colon, the water and feces either moving freely down the colon or being transported out of the colon by matter transportation apparatus 140. The water and feces arrive at speculum 153. Optionally, additional water is provided inside envelope 160 (e.g., using a tube, not shown) to wash the feces down to collection container 157.

In an exemplary embodiment of the invention, speculum 153 is connected to a distal flexible portion 154 leading to a junction, such as T-shaped junction 155. In an alternative embodiment, the feces travel to the end of envelope 160 before traveling down to container 157. Falling into the lower portion of the "T", the feces and water travel downwards via flexible pipe (156) to feces collection tank (157), optionally placed on a scale 158. Scale 158 may be connected to processor/controller 162 of working station 159, which optionally controls operation of system 400 by controlling valve 1622 according to calculations based at least in part on water input data from water input measuring apparatus 401 and/or on matter output data reported by a matter output measuring apparatus 1581, which in this exemplary embodiment is exemplified by scale 158. Optionally, one or both of water ingress speed and weight and/or rate of exhaust are measured. Feedback to a user may be provided, for example, using a visual and/or an audio display.

An aspect of the operation of system 400 may be seen by comparing FIGS. 7A and 7B. An exemplary collection apparatus 165 comprises a water-tight and preferably air-tight disposable envelope 163 having a distal flexible portion 154, a proximal flexible portion 160 and a (preferably vertical) collection sleeve 156. Envelope 163 may be fixed to pipe/endoscope 152 with a fixed (non-sliding) seal 166 and/or be integral with or fixed to a speculum 153. As shown in FIG. 7B, when cleaning head 151 and pipe/endoscope 152 advance up a colon, flexible portion 160 of envelope 163 optionally becomes shorter, compensating for a change in position of the proximal portion of pipe/endoscope 152. Envelope 163 and collection system 165 in general can therefore comprise a closed system operable to insert water into the body through pipe 152 and remove water and feces exiting the body through speculum 153 in a hygienic and convenient manner. Optionally, system 400 measures water input and matter output and/or flow rates and/or pumping power and/or colon pressure (e.g., using a sensor, not shown, on head 151) and optionally uses a controller 162 to record this data and/or to control the system. Optionally, system control includes sending commands to a valve 1622 which controls water input. Optionally, a feedback cycle is set up, which can promote efficient operation and/or protects patient safety.

In an exemplary embodiment of the invention, apparatus 165 is provided as a single element, for example, in kit form.

In use, endoscope tip (151) moves within the GI lumen, advancing and cleaning within the lumen. Endoscope/pipe 152 can be of fixed length. When cleaning head 151 advances in the body, pipe 152 advances along with it, causing length of the proximal portion of pipe 152 outside the body to be reduced. Flexible tube envelope 163, which is optionally extendable and contractible (optionally "accordion" shaped, as shown in the figure), compensates for changes in the length the proximal portion of pipe 152 outside the body, enabling free movement of pipe/endoscope 152, yet seal 166 (which can be sliding or not) maintains hygienic containment of the feces and water. In an exemplary embodiment of the invention, system 400 encapsulates all matter that comes out of the body through speculum 153 and conveys it to tank 157 for disposal.

Additional details regarding colon cleaning systems, which may be used with features described herein, may be found in a co-filed PCT applications by same organizational applicant, filed on same day, in the same receiving office as this application. Much of the above disclosure is directed to descriptions of exemplary embodiments intended for use in cleaning the intestinal tract, but it is to be understood that systems similar constructed and similarly used are expected to be useful in other bodily organs, for example in cleaning stones from a urinary tract or other body duct, the length and diameters of the systems are optionally adapted to the different locations they are used for in the body. Although descriptions provided below are largely couched in terms of exemplary embodiments designed for use in the intestinal track, the inventive embodiments described herein are not necessarily limited to those exemplary embodiments but should be understood to include any cleaning system for use anywhere inside the body which comprises the elements described and/or claimed herein.

It is expected that during the life of a patent maturing from this application many relevant endoscopes will be developed, and the scope of the term "endoscope" is intended to include all such new technologies a priori. Similarly, it is expected that during the life of a patent maturing from this application many relevant tools for cleaning the GI tract will be developed, and the scope of the term "tool", where appropriate in context, is intended to include all such new technologies a priori.

The terms "comprises", "comprising", "includes", "including", "having" and their conjugates mean "including but not limited to".

The term "consisting of means "including and limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

To the extent that section headings are used, they should not be construed as necessarily limiting.

What is claimed is:

1. A system for colonic cleaning, comprising:
   a colon insertion tube having a body sized for insertion and cleaning up to a cecum of a colon; and
   an envelope that collects exhausted matter from the colon comprising:
   a body including a fecal container of at least 2 liters volumes, a distal flexible portion adapted to couple to the body of said colon insertion tube, and
   a proximal flexible portion having a seal adapted to seal to said colon insertion tube; and
   wherein a portion of said envelope extends over said colon insertion tube between the distal flexible portion and the proximal flexible portion, and is axially extendible and contractible so as to change length according to an insertion depth of said colon insertion tube, by movement of the seal along with the colon insertion tube as the insertion depth changes.

2. The system according to claim 1, wherein said envelope is formed of a flexible material.

3. The system according to claim 1, wherein said envelope is an integral piece.

4. The system according to claim 1, wherein said body of the colon insertion tube includes a speculum which defines an inner lumen larger in diameter than an outer diameter of the colon insertion tube.

5. The system according to claim 1, wherein said seal is a sliding seal.

6. The system according to claim 1, wherein said seal is a fixed attachment to said colon insertion tube.

7. The system according to claim 1, including a vertical sleeve connecting to said fecal container.

8. The system according to claim 1, wherein at least one of the distal flexible portion and the proximal flexible portion is includes at least one pleated section.

9. The system according to claim 1, wherein said envelope further comprises a sensor operative to measure an amount of contents of said container.

10. The system according to claim 9, comprising a valve operative to change the flow of a liquid responsive to said measured amount.

11. The system according to claim 9, wherein said sensor is a scale.

12. The system according to claim 10, wherein said envelope further comprises circuitry which controls said valve responsive to said sensor signal, for stopping inflow and/or increasing outflow according to thresholds of allowed differences.

13. The system according to claim 1, wherein:
the colon insertion tube defines an exhaust lumen; and comprising:
an elongate element located within said exhaust lumen and movable axially for at least a distance of 2 cm; and
at least one vane rotatably mounted on said elongate element, to selectively block or unblock part of said lumen.

14. A system according to claim 13, wherein the at least one vane is spring-loaded to open.

15. The system according to claim 1, wherein:
the colon insertion tube comprises an exhaust conduit adapted for insertion into the colon; and comprising:
a rotating exhausting element mounted within said exhaust conduit; and a distal stop for preventing axial distal advance of said rotating exhausting element.

16. The system according to claim 15, wherein said rotating exhausting element comprises a spiral element with axial elasticity.

17. The system according to claim 16, wherein said spiral element is configured to shred fecal matter.

18. The system according to claim 16, wherein said spiral element defines spacings between adjacent coil turns, which spacings are uneven.

19. The system according to claim 16, wherein said spiral element defines a diameter of adjunct coil turns, which diameters are unequal.

20. The system according to claim 1, wherein a length of said colon insertion tube is between 0.5 and 4 meters.

21. The system according to claim 1, wherein said envelope further comprises a portion which covers said colon insertion tube, said portion compensates for changes in the length of said colon insertion tube outside the body, enabling free movement of said colon insertion tube while maintaining containment of feces and water.

22. The system according to claim 1, wherein the portion of said envelope extending over said colon insertion tube between the distal flexible portion and the proximal flexible portion is configured to be mounted on a colonoscope and sealed at a proximal end of the colonoscope.

23. The system according to claim 1, wherein said portion of said envelope that covers said colon insertion tube is axially extendible and contractible so as to change length according to the insertion depth of said colon insertion tube.

24. The system according to claim 1, wherein said portion of said envelope that covers said colon insertion tube is axially extendible and contractible so when said colon insertion tube is inserted in to said colon and extends as said colon insertion tube is extracted from said colon.

25. The system according to claim 1, wherein the envelope is sized and configured to remain external to the colon while the colon insertion tube is inserted to the colon.

26. The system according to claim 1, wherein the body of the colon insertion tube has a length insertable to the colon, and wherein said length is between 1 and 2.5 meters.

27. A system for colonic cleaning, comprising:
a colon insertion tube sized for insertion and cleaning up to a cecum of a colon; and
an envelope that collects exhausted matter from the colon comprising:
a body including a fecal container of at least 2 liters volumes and a proximal flexible portion having a seal adapted to seal to and enclose a portion of said colon insertion tube; wherein the proximal flexible portion is further adapted;
to be mounted on a colonoscope so that the colon insertion tube extends along the colonoscope, and
also seal to a proximal end of the colonoscope.

28. The system according to claim 27, wherein the body of the colon insertion tube has a length insertable to the colon, and wherein said length is between 1 and 2.5 meters.

* * * * *